US010239926B2

United States Patent
Spees

(10) Patent No.: US 10,239,926 B2
(45) Date of Patent: Mar. 26, 2019

(54) COMPOSITIONS AND METHODS FOR VASCULAR PROTECTION AGAINST REPERFUSION INJURY AFTER MYOCARDIAL ISCHEMIA

(71) Applicant: The University of Vermont and State Agriculture College, Burlington, VT (US)

(72) Inventor: Jeffrey Spees, Burlington, VT (US)

(73) Assignee: The University of Vermont and State Agriculture College, Burlington, VT (US)

( * ) Notice: Subject to any disclaimer, the term of this patent is extended or adjusted under 35 U.S.C. 154(b) by 0 days.

(21) Appl. No.: 15/553,505

(22) PCT Filed: Feb. 23, 2016

(86) PCT No.: PCT/US2016/019136
§ 371 (c)(1),
(2) Date: Aug. 24, 2017

(87) PCT Pub. No.: WO2016/137998
PCT Pub. Date: Sep. 1, 2016

(65) Prior Publication Data
US 2018/0237483 A1   Aug. 23, 2018

Related U.S. Application Data

(60) Provisional application No. 62/126,374, filed on Feb. 27, 2015.

(51) Int. Cl.
| | |
|---|---|
| *A61K 38/18* | (2006.01) |
| *A61K 38/22* | (2006.01) |
| *C07K 14/475* | (2006.01) |
| *C07K 14/47* | (2006.01) |
| *C07K 14/705* | (2006.01) |
| *A61K 38/00* | (2006.01) |

(52) U.S. Cl.
CPC ............ *C07K 14/475* (2013.01); *C07K 14/47* (2013.01); *C07K 14/70503* (2013.01); *A61K 38/00* (2013.01); *A61K 38/18* (2013.01)

(58) Field of Classification Search
None
See application file for complete search history.

(56) References Cited

U.S. PATENT DOCUMENTS

| | | |
|---|---|---|
| 5,684,136 A | 11/1997 | Godowski |
| 2009/0221491 A1 | 11/2009 | Neisser-Svae et al. |
| 2012/0157381 A1 | 6/2012 | Spees |

OTHER PUBLICATIONS

Mizuno et al., Clinical and Experimental Pharmacology and Physiology, 38:192-201, 2011.*
Nakamura et al., "Myocardial Protection from Inschemia/Reperfusion Injury by Endogenous and Exogenous HGF", The Journal of Clinical Investigation, Dec. 2000, vol. 106, No. 12, pp. 1511-1519.
Rao et al., "Human Epicardial Cell-Conditioned Medium Contains HGF/IgG Complexes that Phosphorylate RYK and Protect Against Vascular Injury", Cardiovascular Research, May 29, 2015, vol. 107, pp. 277-286.
Zhou et al., "Adult Mouse Epicardium Modulates Myocardial Injury by Secreting Paracrine Factors", The Journal of Clinical Investigation, May 2011, vol. 121, No. 5, pp. 1894-1904.
International Search Report for corresponding PCT Application No. PCT/US16/19136, dated Jun. 27, 2016 (12 pages).
EESR for correlating European application No. 16756189.3 Dated Jul. 2, 2018 (9 pages).

* cited by examiner

*Primary Examiner* — Marianne P Allen
(74) *Attorney, Agent, or Firm* — Tari Mills; Melissa Hunter-Ensor; Greenberg Traurig, LLP

(57) ABSTRACT

As described herein, the present invention features compositions comprising an HGF/IgG complex and methods of using such compositions to reduce ischemic reperfusion injury.

1 Claim, 14 Drawing Sheets
Specification includes a Sequence Listing.

A    HUMAN RIGHT ATRIUM

C    PROGENITOR      EMT

```
                         SEQUENCE LISTING

<160> NUMBER OF SEQ ID NOS: 34

<210> SEQ ID NO 1
<211> LENGTH: 476
<212> TYPE: PRT
<213> ORGANISM: Homo sapiens

<400> SEQUENCE: 1

Met Asp Trp Thr Trp Arg Phe Leu Phe Val Val Ala Ala Ala Thr Gly
1               5                   10                  15

Val Gln Ser Gln Met Gln Val Val Gln Ser Gly Ala Glu Val Lys Lys
            20                  25                  30

Pro Gly Ser Ser Val Thr Val Ser Cys Lys Ala Ser Gly Gly Thr Phe
        35                  40                  45

Ser Asn Tyr Ala Ile Ser Trp Val Arg Gln Ala Pro Gly Gln Gly Leu
    50                  55                  60

Glu Trp Met Gly Gly Ile Ile Pro Leu Phe Gly Thr Pro Thr Tyr Ser
65                  70                  75                  80

Gln Asn Phe Gln Gly Arg Val Thr Ile Thr Ala Asp Lys Ser Thr Ser
                85                  90                  95

Thr Ala His Met Glu Leu Ile Ser Leu Arg Ser Glu Asp Thr Ala Val
            100                 105                 110

Tyr Tyr Cys Ala Thr Asp Arg Tyr Arg Gln Ala Asn Phe Asp Arg Ala
        115                 120                 125

Arg Val Gly Trp Phe Asp Pro Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285
```

```
Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 2
<211> LENGTH: 728
<212> TYPE: PRT
<213> ORGANISM: Homo sapiens

<400> SEQUENCE: 2

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190
```

```
Asn Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
            245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
            355                 360                 365

Asp Pro Asn Ile Arg Val Gly Tyr Cys Ser Gln Ile Pro Asn Cys Asp
            370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
                420                 425                 430

Ser Lys Leu Asn Glu Asn Tyr Cys Arg Asn Pro Asp Asp Asp Ala His
            435                 440                 445

Gly Pro Trp Cys Tyr Thr Gly Asn Pro Leu Ile Pro Trp Asp Tyr Cys
            450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
            515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
            595                 600                 605
```

```
Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725
```

<210> SEQ ID NO 3
<211> LENGTH: 2820
<212> TYPE: DNA
<213> ORGANISM: Homo sapiens

<400> SEQUENCE: 3

```
gggagttcag acctagatct ttccagttaa tcacacaaca aacttagctc atcgcaataa      60
aaagcagctc agagccgact ggctctttta ggcactgact ccgaacagga ttctttcacc     120
caggcatctc ctccagaggg atccgccagc cgtccagca gcaccatgtg ggtgaccaaa     180
ctcctgccag ccctgctgct gcagcatgtc ctcctgcatc tcctcctgct ccccatcgcc     240
atcccctatg cagagggaca aaggaaaaga agaaatacaa ttcatgaatt caaaaaatca     300
gcaaagacta ccctaatcaa aatagatcca gcactgaaga taaaaaccaa aaaagtgaat     360
actgcagacc aatgtgctaa tagatgtact aggaataaag acttccatt cacttgcaag     420
gcttttgttt ttgataaagc aagaaaacaa tgcctctggt tcccccttcaa tagcatgtca     480
agtggagtga aaaagaatt tggccatgaa tttgacctct atgaaaacaa agactacatt     540
agaaactgca tcattggtaa aggacgcagc tacaagggaa cagtatctat cactaagagt     600
ggcatcaaat gtcagccctg gagttccatg ataccacacg aacacagctt tttgccttcg     660
agctatcggg gtaaagacct acaggaaaac tactgtcgaa atcctcgagg ggaagaaggg     720
ggacctggt gtttcacaag caatccagag gtacgctacg aagtctgtga cattcctcag     780
tgttcagaag ttgaatgcat gacctgcaat ggggagagtt atcgaggtct catggatcat     840
acagaatcag gcaagatttg tcagcgctgg gatcatcaga caccacaccg gcacaaattc     900
ttgcctgaaa gatatcccga caagggcttt gatgataatt attgccgcaa tcccgatggc     960
cagccgaggc catggtgcta tactcttgac cctcacaccc gctggagtta ctgtgcaatt    1020
aaaacatgcg ctgacaatac tatgaatgac actgatgttc ctttggaaac aactgaatgc    1080
atccaaggtc aaggagaagg ctacagggc actgtcaata ccatttggaa tggaattcca    1140
tgtcagcgtt gggattctca gtatcctcac gagcatgaca tgactcctga aaatttcaag    1200
tgcaaggacc tacgagaaaa ttactgccga aatccagatg gtctgaatc accctggtgt    1260
tttaccactg atccaaacat ccgagttggc tactgctccc aaattccaaa ctgtgatatg    1320
tcacatggac aagattgtta tcgtgggaat ggcaaaaatt atatgggcaa cttatcccaa    1380
acaagatctg gactaacatg ttcaatgtgg gacaagaaca tggaagactt acatcgtcat    1440
```

```
atcttctggg aaccagatgc aagtaagctg aatgagaatt actgccgaaa tccagatgat    1500
gatgctcatg gaccctggtg ctacacggga atccactca ttccttggga ttattgccct    1560
atttctcgtt gtgaaggtga taccacacct acaatagtca atttagacca tcccgtaata    1620
tcttgtgcca aaacgaaaca attgcgagtt gtaaatggga ttccaacacg aacaaacata    1680
ggatggatgg ttagtttgag atacagaaat aaacatatct gcggaggatc attgataaag    1740
gagagttggg ttcttactgc acgacagtgt ttcccttctc gagacttgaa agattatgaa    1800
gcttggcttg gaattcatga tgtccacgga agaggagatg agaaatgcaa acaggttctc    1860
aatgtttccc agctggtata tggccctgaa ggatcagatc tggttttaat gaagcttgcc    1920
aggcctgctg tcctggatga ttttgttagt acgattgatt tacctaatta tggatgcaca    1980
attcctgaaa agaccagttg cagtgtttat ggctggggct acactggatt gatcaactat    2040
gatggcctat tacgagtggc acatctctat ataatgggaa atgagaaatg cagccagcat    2100
catcgaggga aggtgactct gaatgagtct gaaatatgtg ctggggctga aaagattgga    2160
tcaggaccat gtgaggggga ttatggtggc ccacttgttt gtgagcaaca taaaatgaga    2220
atggttcttg gtgtcattgt tcctggtcgt ggatgtgcca ttccaaatcg tcctggtatt    2280
tttgtccgag tagcatatta tgcaaaatgg atacacaaaa ttattttaac atataaggta    2340
ccacagtcat agctgaagta agtgtgtctg aagcacccac caatacaact gtcttttaca    2400
tgaagatttc agagaatgtg aatttaaaaa tgtcacttac aacaatccta agacaactac    2460
tggagagtca tgtttgttga aattctcatt aatgtttatg ggtgttttct gttgttttgt    2520
ttgtcagtgt tattttgtca atgttgaagt gaattaaggt acatgcaagt gtaataacat    2580
atctcctgaa gatacttgaa tggattaaaa aaacacacag gtatatttgc tggatgataa    2640
agatttcatg ggaaaaaaaa tcaattaatc tgtctaagct gctttctgat gttggtttct    2700
taataatgag taaaccacaa attaaatgtt attttaacct caccaaaaca atttatacct    2760
tgtgtcccta aattgtagcc ctatattaaa ttatattaca tttcaaaaaa aaaaaaaaaa    2820
```

<210> SEQ ID NO 4
<211> LENGTH: 610
<212> TYPE: PRT
<213> ORGANISM: Homo sapiens

<400> SEQUENCE: 4

```
Met Arg Gly Ala Ala Arg Leu Gly Arg Pro Gly Arg Ser Cys Leu Pro
1               5                   10                  15

Gly Ala Arg Gly Leu Arg Ala Pro Pro Pro Pro Leu Leu Leu Leu
            20                  25                  30

Leu Ala Leu Leu Pro Leu Leu Pro Ala Pro Gly Ala Ala Ala Pro
        35                  40                  45

Ala Pro Arg Pro Pro Glu Leu Gln Ser Ala Ser Ala Gly Pro Ser Val
    50                  55                  60

Ser Leu Tyr Leu Ser Glu Asp Glu Val Arg Arg Leu Ile Gly Leu Asp
65                  70                  75                  80

Ala Glu Leu Tyr Tyr Val Arg Asn Asp Leu Ile Ser His Tyr Ala Leu
                85                  90                  95

Ser Phe Ser Leu Leu Val Pro Ser Glu Thr Asn Phe Leu His Phe Thr
            100                 105                 110

Trp His Ala Lys Ser Lys Val Glu Tyr Lys Leu Gly Phe Gln Val Asp
        115                 120                 125
```

-continued

```
Asn Val Leu Ala Met Asp Met Pro Gln Val Asn Ile Ser Val Gln Gly
            130                 135                 140

Glu Val Pro Arg Thr Leu Ser Val Phe Arg Val Glu Leu Ser Cys Thr
145                 150                 155                 160

Gly Lys Val Asp Ser Glu Val Met Ile Leu Met Gln Leu Asn Leu Thr
                165                 170                 175

Val Asn Ser Ser Lys Asn Phe Thr Val Leu Asn Phe Lys Arg Arg Lys
            180                 185                 190

Met Cys Tyr Lys Lys Leu Glu Val Lys Thr Ser Ala Leu Asp Lys
                195                 200                 205

Asn Thr Ser Arg Thr Ile Tyr Asp Pro Val His Ala Ala Pro Thr Thr
210                 215                 220

Ser Thr Arg Val Phe Tyr Ile Ser Val Gly Val Cys Cys Ala Val Ile
225                 230                 235                 240

Phe Leu Val Ala Ile Ile Leu Ala Val Leu His Leu His Ser Met Lys
                245                 250                 255

Arg Ile Glu Leu Asp Asp Ser Ile Ser Ala Ser Ser Ser Ser Gln Gly
                260                 265                 270

Leu Ser Gln Pro Ser Thr Gln Thr Thr Gln Tyr Leu Arg Ala Asp Thr
    275                 280                 285

Pro Asn Asn Ala Thr Pro Ile Thr Ser Ser Leu Gly Tyr Pro Thr Leu
290                 295                 300

Arg Ile Glu Lys Asn Asp Leu Arg Ser Val Thr Leu Leu Glu Ala Lys
305                 310                 315                 320

Gly Lys Val Lys Asp Ile Ala Ile Ser Arg Glu Arg Ile Thr Leu Lys
                325                 330                 335

Asp Val Leu Gln Glu Gly Thr Phe Gly Arg Ile Phe His Gly Ile Leu
            340                 345                 350

Ile Asp Glu Lys Asp Pro Asn Lys Glu Lys Gln Ala Phe Val Lys Thr
            355                 360                 365

Val Lys Asp Gln Ala Ser Glu Ile Gln Val Thr Met Met Leu Thr Glu
370                 375                 380

Ser Cys Lys Leu Arg Gly Leu His His Arg Asn Leu Leu Pro Ile Thr
385                 390                 395                 400

His Val Cys Ile Glu Glu Gly Glu Lys Pro Met Val Ile Leu Pro Tyr
                405                 410                 415

Met Asn Trp Gly Asn Leu Lys Leu Phe Leu Arg Gln Cys Lys Leu Val
                420                 425                 430

Glu Ala Asn Asn Pro Gln Ala Ile Ser Gln Gln Asp Leu Val His Met
            435                 440                 445

Ala Ile Gln Ile Ala Cys Gly Met Ser Tyr Leu Ala Arg Arg Glu Val
450                 455                 460

Ile His Lys Asp Leu Ala Ala Arg Asn Cys Val Ile Asp Asp Thr Leu
465                 470                 475                 480

Gln Val Lys Ile Thr Asp Asn Ala Leu Ser Arg Asp Leu Phe Pro Met
                485                 490                 495

Asp Tyr His Cys Leu Gly Asp Asn Glu Asn Arg Pro Val Arg Trp Met
            500                 505                 510

Ala Leu Glu Ser Leu Val Asn Asn Glu Phe Ser Ser Ala Ser Asp Val
            515                 520                 525

Trp Ala Phe Gly Val Thr Leu Trp Glu Leu Met Thr Leu Gly Gln Thr
530                 535                 540

Pro Tyr Val Asp Ile Asp Pro Phe Glu Met Ala Ala Tyr Leu Lys Asp
```

-continued

```
              545                 550                 555                 560
        Gly Tyr Arg Ile Ala Gln Pro Ile Asn Cys Pro Asp Glu Leu Phe Ala
                        565                 570                 575
        Val Met Ala Cys Cys Trp Ala Leu Asp Pro Glu Glu Arg Pro Lys Phe
                        580                 585                 590
        Gln Gln Leu Val Gln Cys Leu Thr Glu Phe His Ala Ala Leu Gly Ala
                    595                 600                 605
        Tyr Val
            610

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
tttaccttcc agcagcccta                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
cccactgtcc tcatctgaca                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gagcatacag ccccatcact                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
gggtctgaaa gcttggactg                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
gtccgcagtc ttacgaggag                                                   20

<210> SEQ ID NO 10
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 10
tggaggacct ggtagaggaa                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
ctaccctcac tctcccacca                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
gcaccagtgt tttggttcct                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
cacaagatga atggcgtcaa                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
cttccgtgtc tggatgcttt                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
cgggggtgaa tcttgtctaa                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
cctggaccat cccctatttt                                               20
```

```
<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
gtagagatga cgggcctcag                                                     20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
tttccaaggt ggctggtaac                                                     20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
ggggagactt ggatgagaca                                                     20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
agcaagagga gccagacaaa                                                     20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
acgtgctcag ttttgcctct                                                     20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
cagttttgtg ttggcattgg                                                     20

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide
```

```
<400> SEQUENCE: 23
gaagaggaca gcactgcct                                              19

<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 24
ctgataggac attgttagca ta                                          22

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 25
aagaaccgaa gtcccaggag aaagg                                       25

<210> SEQ ID NO 26
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 26
agatttcaga ggcgttctaa aactca                                      26

<210> SEQ ID NO 27
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 27
gacgggtcac tatctgtgca ac                                          22

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 28
agacatcgca ctgactgaga ac                                          22

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
ctgggaaacc ccaacctatt                                             20

<210> SEQ ID NO 30
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
gctgcctggt ggaataagaa                                               20

<210> SEQ ID NO 31
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 31
ggactgctct ggcaacccag tgc                                           23

<210> SEQ ID NO 32
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 32
catctgactc cgggtcattt gc                                            22

<210> SEQ ID NO 33
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 33
gctgagtacg tcgtggagt                                                19

<210> SEQ ID NO 34
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 34
caccactgac acgttggca                                                19
```

COMPOSITIONS AND METHODS FOR VASCULAR PROTECTION AGAINST REPERFUSION INJURY AFTER MYOCARDIAL ISCHEMIA

CROSS REFERENCE TO RELATED APPLICATIONS

This application is the U.S. national phase application, pursuant to 35 U.S.C. § 371, of PCT International Application Ser. No.: PCT/US2016/019136, filed Feb. 23, 2016, designating the United States and published in English, which claims benefit of U.S. Provisional Application Ser. No. 62/126,374, filed Feb. 27, 2015, the contents of which are incorporated herein by reference in their entirety.

STATEMENT OF RIGHTS TO INVENTIONS MADE UNDER FEDERALLY SPONSORED RESEARCH

This work was supported by the following grants from the National Institutes of Health, Grant Nos: HL077570 and HL085210. The government has certain rights in the invention.

BACKGROUND OF THE INVENTION

Despite recent advances in treating ischemic injuries, myocardial infarction is still the leading cause of death for both, women and men. In the United States alone, each year more than 920,000 myocardial infarctions occur of which about 38% result in death. However, many of those who survive a myocardial infarction will be disabled by some loss in cardiac function. The overall economic cost of cardiovascular disease, which includes coronary heart disease, hypertensive disease, heart failure and stroke, are more than twice the amount of cancer in the U.S. and reached an estimated $448.5 billion in 2008.

Vascular perfusion is a key aspect of cardiac function and patients with myocardial ischemia often benefit from restoration of blood flow to occluded vessels by percutaneous coronary intervention (PCI) or thrombolytics (e.g., tissue plasminogen activator (TPA)). Notably, however, re-canalized macroscopic vessels do not always lead to improved microvascular perfusion. This phenomenon is described as "no re-flow" or "low re-flow". Importantly, the extent of no re-flow is a major determinant of infarct expansion after myocardial infarction. No re-flow may result from destruction of microscopic vessels, which in the present study was termed "vascular rhexis" or other factors such as microemboli, inflammation, release of toxic cellular metabolites, or oxidative stress that cause endothelial cell dysfunction and induce microvascular leaks. Historically, many studies have attempted to reduce infarct size and improve cardiac function through replacement of damaged myocytes and vascular cells by stem/progenitor cell transplantation. Few studies, however, have focused on protection of microvascular endothelial cells at the time of reperfusion to reduce vascular leak and infarct expansion after myocardial infarction. Accordingly, improved methods of treating ischemic reperfusion injury are urgently required.

SUMMARY OF THE INVENTION

As described below, the present invention features compositions comprising an HGF/IgG complex and methods of using such compositions to reduce ischemic reperfusion injury.

In one aspect, the invention provides a composition containing an isolated HGF/IgG complex. In one embodiment the HGF/IgG complex does not involve an antibody-antigen interaction.

In another aspect, the invention provides a pharmaceutical composition for reducing ischemic reperfusion injury, the composition containing an isolated HGF/IgG complex and a pharmaceutically acceptable excipient. In one embodiment the HGF/IgG complex does not involve an antibody-antigen interaction. In another embodiment the HGF/IgG complex is purified from human epicardial-derived cell-conditioned medium. In yet another embodiment, the HGF/IgG complex contains a subunit of HGF having a molecular mass of less than about 90 kDa. In a particular embodiment, the HGF/IgG complex contains a subunit of HGF having a molecular mass of about 65 kDa and/or a subunit of HGF having a molecular mass of about 32 kDa. In still another embodiment, the HGF and/or the IgG is recombinantly expressed.

In one aspect, the invention features an HGF/IgG complex produced by contacting isolated HGF or a subunit thereof with IgG, thereby forming an HGF/IgG complex. In one embodiment, the HGF/IgG complex does not involve an antibody-antigen interaction. In another embodiment, the invention provides a complex, where the HGF or subunit thereof or IgG or fragment thereof is recombinantly expressed. In another embodiment the HGF subunit is expressed as an about 65 kDa or an about 32 kDa protein.

In one aspect, the invention features an HGF/IgG complex produced by purifying an HGF/IgG complex from conditioned media obtained from a culture of epicardial-derived cells. In one embodiment the HGF/IgG complex does not involve an antibody-antigen interaction.

In another aspect, the invention provides a method for enhancing vascular integrity following myocardial ischemia with reperfusion, the method involving contacting one or more vascular endothelial cells with an isolated HGF/IgG complex prior to, during or following myocardial ischemia with reperfusion, thereby increasing vascular integrity relative to a reference following myocardial ischemia with reperfusion.

In yet another aspect, the invention provides a method for reducing vascular permeability following myocardial ischemia with reperfusion, the method involving contacting one or more vascular endothelial cells with an isolated HGF/IgG complex prior to, during or following myocardial ischemia with reperfusion, thereby reducing vascular permeability relative to a reference following myocardial ischemia with reperfusion.

In still another aspect, the invention features a method for reducing cell damage or cell death following myocardial ischemia with reperfusion, the method involving contacting one or more cells with an isolated HGF/IgG complex prior to, during or following ischemia with reperfusion, thereby reducing cell damage or cell death relative to a reference following myocardial ischemia with reperfusion. In one embodiment, the cell death occurs during hypoxia. In various embodiments the HGF/IgG complex does not involve an antibody-antigen interaction. In another embodiment, the cell is an endothelial cell, smooth muscle cell, fibroblast, cardiac myocyte, skeletal muscle cell, peripheral neuron, CNS neuron, astrocyte, oligodendrocyte, pulmonary epithelial cell, liver epithelial cell, or kidney epithelial cell. In various embodiments, the cell is in vitro or in vivo. In particular embodiments, the cell is a human cell.

In one aspect, the invention provides a method for reducing vascular permeability following myocardial ischemia with reperfusion in a subject, the method involving administering to the subject a composition containing an HGF/IgG complex prior to, during or following myocardial ischemia with reperfusion relative to a reference, thereby reducing vascular permeability following myocardial ischemia with reperfusion in the subject. In one embodiment, the method increases vascular integrity in the subject.

In one aspect, the invention features a method for reducing cell damage or cell death following myocardial ischemia with reperfusion in a subject, the method involving administering to the subject a composition containing an HGF/IgG complex prior to, during or following myocardial ischemia with reperfusion, thereby reducing cell damage or cell death relative to a reference following myocardial ischemia with reperfusion. In various embodiments, the subject is a human subject. In various embodiments, the composition contains an effective amount of an HGF/IgG complex. In various embodiments the HGF/IgG complex does not comprise an antibody-antigen interaction. In particular embodiments, the composition phosphorylates RYK.

In one aspect, the invention provides a kit for reducing vascular permeability following myocardial ischemia with reperfusion, the kit containing a purified HGF/IgG complex. In one embodiment the HGF/IgG complex does not comprise an antibody-antigen interaction.

In one aspect, the invention provides a method for enhancing vascular integrity following myocardial ischemia with reperfusion, the method involving activating receptor-like tyrosine kinase (RYK) by contacting the cell with isolated HGF/IgG complex. In one embodiment, the HGF/IgG complex does not comprise an antibody-antigen interaction.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Immunoglobulin G (IgG)" is meant a protein or fragment thereof having at least about 85% identity to NCBI Accession No. AAA02914.1 and having HGF binding activity. An exemplary full-length human IgG polypeptide is provided below.

```
  1  mdwtwrflfv vaaatgvqsq mqvvqsgaev kkpgssvtvs ckasggtfsn yaiswvrqap
 61  gqglewmggi iplfgtptys qnfqgrvtit adkststahm elislrsedt avyycatdry
121  rqanfdrarv gwfdpwgqgt lvtvssastk gpsvfplaps skstsggtaa lgclvkdyfp
181  epvtvswnsg altsgvhtfp avlqssglys lssvvtvpss slgtqtyicn vnhkpsntkv
241  dkkvepkscd kthtcppcpa pellggpsvf lfppkpkdtl misrtpevtc vvvdvshedp
301  evkfnwyvdg vevhnaktkp reeqynstyr vvsvltvlhq dwlngkeykc kvsnkalpap
361  iektiskakg qprepqvytl ppsrdeltkn qvsltclvkg fypsdiavew esngqpenny
421  kttppvldsd gsfflysklt vdksrwqqgn vfscsvmhea lhnhytqksl slspgk
```

By "Hepatocyte Growth Factor (HGF)" is meant a protein or fragment thereof having at least about 85% identity to NCBI Accession No. NP_000592.3 that binds IgG. An exemplary full-length human HGF polypeptide is provided below.

```
  1  mwvtkllpal llqhvllhll llpiaipyae gqrkrrntih efkksakttl ikidpalkik
 61  tkkvntadqc anrctrnkgl pftckafvfd karkqclwfp fnsmssgvkk efghefdlye
121  nkdyirncii gkgrsykgtv sitksgikcq pwssmipheh sflpssyrgk dlqenycrnp
181  rgeeggpwcf tsnpevryev cdipqcseve cmtcngesyr glmdhtesgk icqrwdhqtp
241  hourhkflpery pdkgfddnyc rnpdgqprpw cytldphtrw eycaiktcad ntmndtdvpl
301  etteciqgqg egyrgtvnti wngipcqrwd sqyphehdmt penfkckdlr enycrnpdgs
361  espwcfttdp nirvgycsqi pncdmshgqd cyrgngknym gnlsqtrsgl tcsmwdknme
421  dlhrhifwep dasklnenyc rnpdddahgp wcytgnplip wdycpisrce gdttptivnl
481  dhpviscakt kqlrvvngip trtnigwmvs lryrnkhicg gslikeswvl tarqcfpsrd
541  lkdyeawlgi hdvhgrgdek ckqvlnvsql vygpegsdlv lmklarpavl ddfvstidlp
601  nygctipekt scsvygwgyt glinydgllr vahlyimgne kcsqhhrgkv tlneseicag
```

```
661  aekigsgpce gdyggplvce qhkmrmvlgv ivpgrgcaip nrpgifvrva yyakwihkii
721  ltykvpqs
```

In one embodiment, an HGF fragment is a 29-35 kDa subunit (e.g., 31, 32, 33 kDa) or a 59-70 kDa subunit (e.g., 63, 64, 65, 66, 67 kDa subunit, Nakamura et al., 1989, Nature 342:440-443).

By "Hepatocyte Growth Factor (HGF) polynucleotide" is meant a nucleic acid molecule encoding an HGF polypeptide or fragment thereof. An exemplary human HGF polynucleotide is provided at NCBI Accession No. NM_000601, which is reproduced below.

```
   1  gggagttcag acctagatct ttccagttaa tcacacaaca aacttagctc atcgcaataa
  61  aaagcagctc agagccgact ggctcttta ggcactgact ccgaacagga ttctttcacc
 121  caggcatctc ctccagaggg atccgccagc ccgtccagca gcaccatgtg ggtgaccaaa
 181  ctcctgccag ccctgctgct gcagcatgtc ctcctgcatc tcctcctgct ccccatcgcc
 241  atccctatg cagagggaca aaggaaaaga agaaatacaa ttcatgaatt caaaaaatca
 301  gcaaagacta ccctaatcaa aatagatcca gcactgaaga taaaaaccaa aaaagtgaat
 361  actgcagacc aatgtgctaa tagatgtact aggaataaag gacttccatt cacttgcaag
 421  gcttttgttt ttgataaagc aagaaaacaa tgcctctggt tccccttcaa tagcatgtca
 481  agtggagtga aaaagaatt tggccatgaa tttgacctct atgaaaacaa agactacatt
 541  agaaactgca tcattggtaa aggacgcagc tacaagggaa cagtatctat cactaagagt
 601  ggcatcaaat gtcagccctg gagttccatg ataccacacg aacacagctt tttgccttcg
 661  agctatcggg gtaaagacct acaggaaaac tactgtcgaa atcctcgagg ggaagaaggg
 721  ggaccctggt gtttcacaag caatccagag gtacgctacg aagtctgtga cattcctcag
 781  tgttcagaag ttgaatgcat gacctgcaat ggggagagtt atcgaggtct catggatcat
 841  acagaatcag gcaagatttg tcagcgctgg gatcatcaga caccacaccg gcacaaattc
 901  ttgcctgaaa gatatcccga caagggcttt gatgataatt attgccgcaa tcccgatggc
 961  cagccgaggc catggtgcta tactcttgac cctcacaccc gctgggagta ctgtgcaatt
1021  aaaacatgcg ctgacaatac tatgaatgac actgatgttc ctttggaaac aactgaatgc
1081  atccaaggtc aaggagaagg ctacagggga ctgtcaata ccatttggaa tggaattcca
1141  tgtcagcgtt gggattctca gtatcctcac gagcatgaca tgactcctga aaatttcaag
1201  tgcaaggacc tacgagaaaa ttactgccga aatccagatg gtctgaatc accctggtgt
1261  tttaccactg atccaaacat ccgagttgc tactgctccc aaattccaaa ctgtgatatg
1321  tcacatggac aagattgtta tcgtgggaat ggcaaaaatt atatgggcaa cttatcccaa
1381  acaagatctg gactaacatg ttcaatgtgg gacaagaaca tggaagactt acatcgtcat
1441  atcttctggg aaccagatgc aagtaagctg aatgagaatt actgccgaaa tccagatgat
1501  gatgctcatg gaccctggtg ctacacggga aatccactca ttccttggga ttattgccct
1561  atttctcgtt gtgaaggtga taccacacct acaatagtca atttagacca tcccgtaata
1621  tcttgtgcca aaacgaaaca attgcgagtt gtaaatggga ttccaacacg aacaaacata
1681  ggatggatgg ttagtttgag atacagaaat aaacatatct gcggaggatc attgataaag
1741  gagagttggg ttcttactgc acgacagtgt ttcccttctc gagacttgaa agattatgaa
1801  gcttggcttg gaattcatga tgtccacgga agaggagatg agaaatgcaa acaggttctc
1861  aatgtttccc agctggtata tggccctgaa ggatcagatc tggttttaat gaagcttgcc
1921  aggcctgctg tcctggatga ttttgttagt acgattgatt tacctaatta tggatgcaca
```

```
-continued
1981   attcctgaaa agaccagttg cagtgtttat ggctggggct acactggatt gatcaactat 2041   gatggcctat tacgagtggc acatctctat ataatgggaa atgagaaatg cagccagcat 2101   catcgaggga aggtgactct gaatgagtct gaaatatgtg ctggggctga aaagattgga 2161   tcaggaccat gtgaggggga ttatggtggc ccacttgttt gtgagcaaca taaaatgaga 2221   atggttcttg gtgtcattgt tcctggtcgt ggatgtgcca ttccaaatcg tcctggtatt 2281   tttgtccgag tagcatatta tgcaaaatgg atacacaaaa ttattttaac atataaggta 2341   ccacagtcat agctgaagta agtgtgtctg aagcacccac caatacaact gtcttttaca 2401   tgaagatttc agagaatgtg gaatttaaaa tgtcacttac aacaatccta agacaactac 2461   tggagagtca tgtttgttga aattctcatt aatgtttatg ggtgttttct gttgtttgt 2521   ttgtcagtgt tattttgtca atgttgaagt gaattaaggt acatgcaagt gtaataacat 2581   atctcctgaa gatacttgaa tggattaaaa aaacacacag gtatatttgc tggatgataa 2641   agatttcatg ggaaaaaaaa tcaattaatc tgtctaagct gctttctgat gttggtttct 2701   taataatgag taaaccacaa attaaatgtt attttaacct caccaaaaca atttatacct 2761   tgtgtcccta aattgtagcc ctatattaaa ttatattaca tttcaaaaaa aaaaaaaaaa
```

By "phospho-Receptor-Like Tyrosine Kinase (RYK)" is meant a protein or fragment thereof having at least about 85% identity to NCBI Accession No. NP_001005861 and having RYK antibody binding activity. An exemplary full-length human RYK polypeptide is provided below.

```
  1   mrgaarlgrp grsclpgarg lrappppll lllallpllp apgaaaapap rppelqsasa 61   gpsvslylse devrrligld aelyyvrndl ishyalsfsl lvpsetnflh ftwhakskve 121   yklgfqvdnv lamdmpqvni svqgevprtl svfrvelsct gkvdsevmil mqlnltvnss 181   knftvlnfkr rkmcykklee vktsaldknt srtiydpvha apttstrvfy isvgvccavi 241   flvaiilavl hlhsmkriel ddsisassss gglsqpstqt tqylradtpn natpitsslg 301   yptlriekhd lrsvtlleak gkvkdiaisr eritlkdvlq egtfgrifhg ilidekdpnk 361   ekqafvktvk dqaseiqvtm mltescklrg lhhrnllpit hvcieegekp mvilpymnwg 421   nlklflrqck lveannpqai sqqdlvhmai qiacgmsyla rrevihkdla arncviddtl 481   qvkitdnals rdlfpmdyhc lgdnenrpvr wmaleslvnn efssasdvwa fgvtlwelmt 541   lgqtpyvdid pfemaaylkd gyriaqpinc pdelfavmac cwaldpeerp kfqqlvqclt 601   efhaalgayv
```

By "ameliorate" is meant decrease, suppress, attenuate, diminish, arrest, or stabilize the development or progression of a disease. In one embodiment, a composition of the invention ameliorates myocardial ischemic reperfusion injury.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid. In one embodiment, the compositions and methods employ an HGF analog.

By "complex" is meant two or more associated proteins or fragments thereof. A complex may be formed, for example, by two proteins that bind, interact or otherwise share some mutual affinity (e.g., electrostatic). In one embodiment, a complex comprises HGF or a fragment thereof in association with an IgG or a fragment thereof (e.g., an HGF/IgG complex). In certain embodiments, the interaction of the HGF or a fragment thereof and an IgG or a fragment thereof is not an antibody-antigen interaction and/or does not involve specific binding via one or more complementary determining regions of an antibody variable domain. In particular embodiments, the HGF or a fragment thereof interacts with an Fc domain of an IgG or a fragment thereof.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include any disease or injury that results in a reduction in cell number or biological function, including diabetic retinopathy, peripheral artery disease, ischemic injury, stroke, myocardial infarction, or any other ischemic event that causes tissue damage.

By "effective amount" is meant the amount of an agent required to ameliorate the symptoms of a disease relative to an untreated patient. In one embodiment, compositions of the invention comprise an effective amount of an isolated and/or purified HGF/IgG complex used to practice the present invention for therapeutic treatment of ischemic injury. An effective amount varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, 85%, 90%, 95%, or more of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids. In one embodiment, an HGF fragment is a 29-35 kDa subunit (e.g., 31, 32, 33 kDa) or a 59-70 kDa subunit (e.g., 63, 64, 65, 66, 67 kDa subunit) as measured by SDS PAGE.

By "increase" is meant to alter positively by at least 5%. An alteration may be by 5%, 10%, 25%, 30%, 50%, 75%, or even by 100%.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis. When a cellular factor is "isolated" from a cultured epicardial progenitor cell the cellular factor is typically separated from cells and cellular debris. It need not be purified to homogeneity. In fact, the composition comprising an isolated cellular factor typically comprises any number of cellular factors whose presence contributes to the biological activity (e.g., growth promoting, survival promoting, or proliferation promoting activity) of the composition. In one embodiment, a composition of the invention comprises or consists of conditioned media from which cells and cellular debris have been removed.

In particular embodiments, an isolated HGF/IgG complex is purified from conditioned cell media or from a recombinant cell and the resulting HGF/IgG complex is at least 65%, 75%, 85%, 90%, 95% or about 100% purified.

In other embodiments, purified recombinant HGF is combined with IgG isolated and/or purified from human sources or other mammalian sources (i.e. rat, mouse, rabbit, pig, goat), or, recombinant IgG. In this manner, the HGF and IgG complexes may be assembled by various means such as concentration by filtration, centrifugation, column chromatography, changes in temperature or density, or by effectively increasing concentration through addition of particular molecules such as dextran sulphate or polyethylene glycol as is standard in the art in methods associated with developing probes for in situ hybridization. Alternatively, more simple means of forming HGF/IgG complexes may be employed such as through altering the effective concentrations of HGF, IgG, or both in a given mixture by addition of either molecule.

By "marker" is meant any protein or polynucleotide having an alteration in expression level or activity that is associated with a developmental state, condition, disease, or disorder.

As used herein, "obtaining" as in "obtaining an agent" includes synthesizing, purchasing, or otherwise acquiring the agent.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reduce" is meant to alter negatively by at least 5%. A reduction may be by 5%, 10%, 25%, 30%, 50%, 75%, or even by 100%. In particular, vascular permeability may be reduced relative to a reference (e.g., untreated control vessel) by at least about 5%, 10%, 25%, 30%, 50%, 75%, or even by 100%.

By "increase" is meant to alter positively by at least 5%. An increase may be by 5%, 10%, 25%, 30%, 50%, 75%, or even by 100%. In particular, vascular integrity may be increased relative to a reference by at least about 5%, 10%, 25%, 30%, 50%, 75%, or even by 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "repair" is meant to ameliorate damage or disease in a tissue or organ.

By "tissue" is meant a collection of cells having a similar morphology and function.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By "vascular integrity" is meant maintenance of fluid flow in a vessel without leakage. Exemplary vessels include arteries, veins, capillaries, and microvessels.

By "vascular permeability" is meant leakage of blood or another bodily fluid from a vessel into the surrounding environment.

Unless specifically stated or obvious from context, as used herein, the term "or" is understood to be inclusive. Unless specifically stated or obvious from context, as used herein, the terms "a", "an", and "the" are understood to be singular or plural.

Any compositions or methods provided herein can be combined with one or more of any of the other compositions and methods provided herein.

BRIEF DESCRIPTION OF THE DRAWINGS

FIGS. 1A-1E show the isolation of adult human epicardial progenitor-like cells undergoing epithelial to mesenchymal transformation into precursor cells. FIG. 1A is an image depicting immunohistochemistry of a section of right atrial appendage from a human donor showing a single layer of keratin-positive epicardial cells. Scale bar=100 μM. FIG. 1B is two images showing an explant culture of right atrial appendage to generate feeder layer (left); Formation of floating spheroids and bunches of cells following switch to medium that favors the growth of stem/progenitor cells (right). FIG. 1C shows two images of maintenance of epicardial progenitor-like cells with epithelial phenotype on uncoated dishes (left), followed by epithelial to mesenchymal transformation at 3 days after incubation of epicardial progenitor cells in medium containing 10% FBS (right). FIG. 1D is two images that show that epicardial progenitor-like cells expressed keratins (epithelial intermediate filament proteins) (left) while precursors derived by epithelial to mesenchymal transformation expressed vimentin (red) but not keratin (green) (right). FIG. 1E shows an agarose gel of—amplification products of RNA from the epicardial cell population after epithelial to mesenchymal transformation and 1 or 2 weeks of culture in medium containing 10% FCS respectively. FIGS. 1B-1D, Scale bar=50 μM. Note: No RT=No RT for GAPDH. EMT: Epithelial to Mesenchymal Transformation.

FIGS. 2A-2D show the time course of epicardial progenitor-like cell formation directly from human epicardial explant. Note that this time course pertains to isolation method #2 for human epicardial derived cells. FIG. 2A shows an image of an epicardial cell outgrowth from epicardial explant generated by dissecting surface epicardial cell layer from right atrial appendage removed during bypass surgery. Outgrowth occurred over 7 days. Note epithelial morphology of cell monolayer. FIG. 2B is an image of an epicardial cell monolayer 1 d after switching medium to adult stem/progenitor expansion medium (see Methods). FIG. 2C depicts an image showing an epicardial cell monolayer 3 d after switching medium to adult stem/progenitor expansion medium. Note refractile cells beginning to round up. FIG. 2D shows an image of an epicardial cell monolayer 4 days after switching medium to adult stem/progenitor expansion medium. Note the formation of "bunches of grapes" due to epicardial progenitor-like cells adhering to each other and growing upward in the culture dish (within yellow dashes). As with isolation method #1, the bunches of progenitor cells pictured in FIG. 2D could be gathered and then transferred to a medium containing 10% FCS to induce epithelial to mesenchymal transformation. Scales bars=50 μM.

FIGS. 3A-3C show the characterization of epicardial and precursor markers of the isolated human cells. FIG. 3A shows four images of immunocytochemistry for epicardial transcription factors: WT1 (top left), TCF21 (top right), GATA4 (bottom left) and RALDH2 (bottom right). FIG. 3B depicts an agarose gel showing that several transcription factors associated with cardiac development were down-regulated in epicardial progenitor-like cells during epithelial to mesenchymal transformation into precursor cells, while others such as smooth muscle actin (SMA) and von Willebrand Factor (vWF) were upregulated. Left lane shows amplification from RNA of progenitor-like cells "EPI" pictured in (FIG. 1C). Middle and right lanes show amplification of RNA from cells after epithelial to mesenchymal transformation and 1 or 2 weeks of culture. Note: the lower fuzzy bands in the gel data for GATA5, Isl-1, and Tbx5 are primer dimers. FIG. 3C depicts three images showing that at 2 weeks after epithelial to mesenchymal transformation, some precursor cells expressed markers of smooth muscle cells (smooth muscle myosin, SMM) or endothelial cells (von Willebrand Factor, vWF). Other cells expressed fibroblast markers such as prolyl-4-hydroxylase (Fibro). Scale bar=100 pM.

FIG. 5A depicts two representative immunofluorescence images showing the extent of FITC-albumin extravasation from an uninjured blood vessel in the right ventricle (RV) (Top) and from an injured left ventricle (LV) vessel (Bottom). Dashed white line indicates infarct border at 24 hours after reperfusion. FIG. 5B is a graph showing that treatment with 30× human epicardial-derived cell-conditioned medium significantly decreased extravasation of FITC-Albumin in the left ventricle wall of rats, 24 hours after reperfusion (n=5 animals per group). In each group, treatment animals are calculated as % of sham. FIG. 5C depicts a Western blot image of 3 representative animals per group showing lower levels of phospho-VE-Cadherin ($pY^{658}$) and higher levels of CD31 in heart homogenates from human epicardial-derived cell-conditioned medium-treated rats compared with minimum essential media (MEM)-treated rats. Note: α smooth muscle actin (α SMA) levels were similar in both treatment groups. (Bottom) Quantification of western blot bands from FIG. 5C. The levels of phospho-VE-Cadherin were higher in MEM (control) vs human epicardial-derived cell-conditioned medium (n=3) and CD31 levels were higher in heart homogenates of human epicardial-derived cell-conditioned medium-treated rats compared with MEM-treated rats (n=3). GM: Growth Medium; Con Conditioned Medium: Control human epicardial-derived cell-conditioned medium; PD: Pull down; Con IgG: Control IgG. * p≤0.05. Scale bar=100 μM.

FIG. 7A is a graph showing that at 72 hours after reperfusion, there was no difference in FITC extravasation as measured by FITC-albumin (n=6 animals per group, p=0.08). FIG. 7B is a graph depicting that myocyte survival in the left ventricle (LV) at 24 hours was determined by assay of left ventricle residual creatine kinase (CK) activity. There was no difference in the level of myocyte survival as indicated by residual creatine kinase activity between the MEM and human epicardial-derived cell-conditioned medium treatment groups at 24 hours (n=5 animals per group, p=0.74).

FIG. 8A is a graph showing that human epicardial-derived cell-conditioned medium protected cultured primary human coronary artery endothelial cells for 48 hours under simulated ischemia, as measured by MTS assay (n=5 donors). Data are mean±S.D. FIG. 8B is a graph showing that human epicardial-derived cell-conditioned medium protected cultured human microvascular endothelial cells for 48 hours under simulated ischemia, as measured by CyQuant assay (n=3 donors). Data are mean±S.D. In both experiments, survival of cells in growth medium (GM) was considered as 100%. FIG. 8C shows a membrane of a receptor tyrosine kinase (RTK) array demonstrating that 30 min exposure to 1× human epicardial-derived cell-conditioned medium induced phosphorylation of multiple growth factor receptors of coronary artery endothelial cells compared with MEM treatment. FIG. 8D shows a graph providing HGF ELISA data for 5 different human epicardial-derived cell-conditioned medium donors (D1-D5), measurements in duplicate. FIG. 8E depicts a graph showing that pull down of HGF from human epicardial-derived cell-conditioned medium with an HGF-specific antibody (2 μg/ml) decreased human epicardial-derived cell-conditioned medium-mediated protection of microvascular endothelial cells during simulated ischemia (48 hours) compared to pull down with a non-specific IgG antibody. FIG. 8F is a graph showing that, in contrast, pull-down of stromal cell-derived factor 1 (SDF-1), angiopoietin 1 (ANG1) or vascular endothelial growth factor A (VEGFA) did not alter protection of microvascular endothelial cells (all antibodies used at 2 μg/ml). Cell numbers were determined by CyQuant assay (dye binding of nuclei acids). Data are mean±S.D. *p≤0.05,  p≤0.01, * p≤0.001. Scale bar=100 μM.

FIG. 11A is a graph showing that pull down of HGF with Protein A Sepharose beads led to a 32% decrease in HGF from 30× human epicardial-derived cell-conditioned medium as measured by ELISA (n=3). FIG. 11B depicts a line graph showing that loss of HGF from human epicardial-derived cell-conditioned medium corresponded to increasing concentration of human epicardial-derived cell-conditioned medium. Solid line=human epicardial-derived cell-conditioned medium, dashed line=human epicardial-derived cell-conditioned medium+non-specific polyclonal IgG. p≤0.05 at 30×. FIG. 11C is a graph showing quantification of HGF after dissociation from Sepharose beads with deoxycholate. FIG. 11D shows an EMSA (electrophoretic mobility shift assay) demonstrating the change in mobility of HGF when complexed with IgG. Human IgG (lane 1) migrates towards the anode at a much slower rate at pH 6.7 compared with human HGF (lane 3). A simple mixture of the 2 proteins (free) did not affect their individual mobilities (lane 3). However, HGF and IgG complexes formed upon concentration, resulted in a band shift for both proteins as a result of altered mobility (lane 4).

FIG. 12A depicts two images and a gel showing stable producer cell lines and purification of bioactive recombinant human HGF. (Left, Top) Phase images of HEK 293 cells with genomic integration of pIRES-puro vector expressing human HGF-His tag-F2A-GFP. (Left, Bottom) epifluorescence image showing GFP expression (FITC channel). (Right) Gel electrophoresis illustrating purification of HGF. Lane 1, Electrophoresis of eluted material under non-reducing conditions demonstrated purity and molecular weight of single chain pro-HGF (90 kDa). Gel stained with Coomassie Brilliant Blue. Lane 2, Purified protein run under reducing conditions (beta-mercaptoethanol) demonstrated the active heterodimer of human HGF (see bands at 65 kDa and 32 kDa). FIG. 12B is a graph showing that CyQuant assay demonstrated enhanced protective effects of HGF/IgG complexes when compared with free HGF (alone) or free HGF with IgG (Free, unconcentrated factors). For greater detail, please refer to Methods. Cell number was assayed after 48 hours of simulated ischemia (MEM, 68.52%±4.73 of HGF; free HGF alone, 100%±7.27; free HGF with IgG [Free], 113.65%±3.117.27 of HGF; HGF with IgG (Complex), 169.034%±4.004 of HGF (n=4 for all). Free HGF with IgG (Free) conferred protection ($p \leq 0.01$ vs. MEM). However, HGF/IgG complexes (Complex) protected better than did free HGF with IgG (Free) ($p \leq 0.001$). There were greater cell numbers in cultures maintained under hypoxic conditions and treated with complex relative to untreated cell cultures. Without wishing to be bound by theory, this difference is attributed to increased cell death. FIG. 12C depicts a membrane showing treatment of coronary endothelial cells with HGF/IgG complexes (Complex, Top), free HGF and IgG (Free, Middle) or MEM (Bottom) affected the level of phosphorylation for receptor-like tyrosine kinase (RYK), but not c-Met. Positive control signal (pos-ctrl) has been included for each membrane to compare for normalization. FIG. 12D is a graph showing that blocking receptor-like tyrosine kinase (RYK) reduced protection conferred by HGF/IgG complexes ($p \leq 0.01$, n=2) but not protection by free HGF with IgG (p=0.09, n=2). Note: Coronary artery endothelial cells were incubated under simulated ischemia for 24 hours. FIG. 12E is a graph showing that intra-arterial treatment with HGF/IgG complexes significantly decreased FITC-albumin extravasation in the left ventricle wall of rats at 24 hours after reperfusion (MEM, n=4; free HGF with IgG [Free], n=8; HGF/IgG complexes [Complex], n=11; $p \leq 0.01$). FIGS. 12F1, 12F2, and 12F3 depict three images of a fluorescent micrograph showing localization of His-HGF outside blood vessels (by anti-His antibody). HGF/IgG complexes were localized to large blood vessels (FIGS. 12F1 and 12F2) and to the microvasculature (FIG. 12F3). Arrows: His-HGF colocalized with capillaries (lectin). Data are mean±S.D. *$p \leq 0.001$,  $p \leq 0.01$. Scale bar=100 μM, 50 μM (6F").

DETAILED DESCRIPTION OF THE INVENTION

Figure 1:
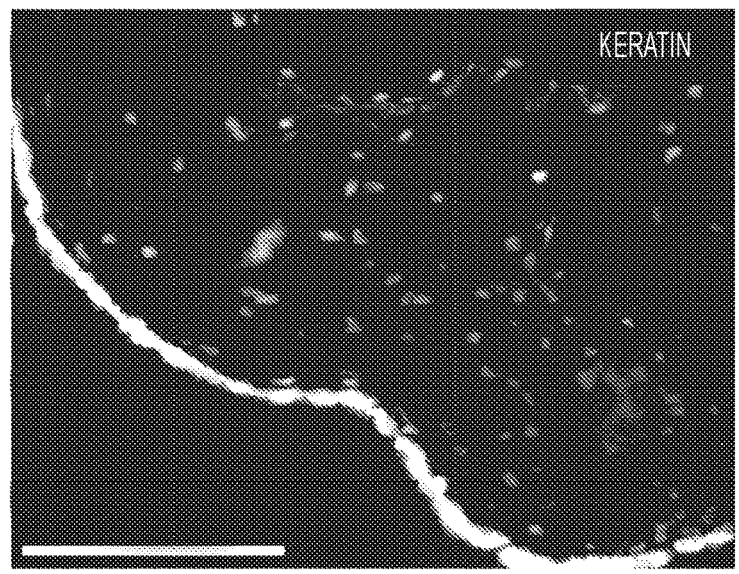
Figure 1:
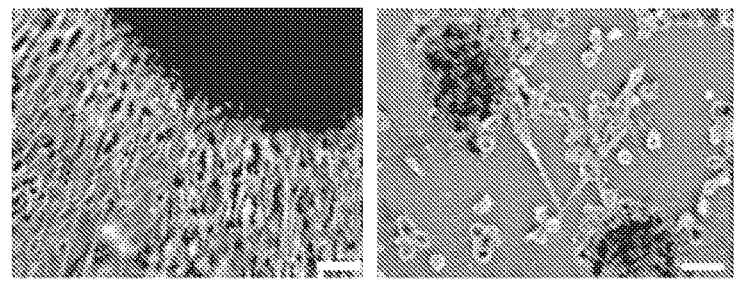
Figure 1:
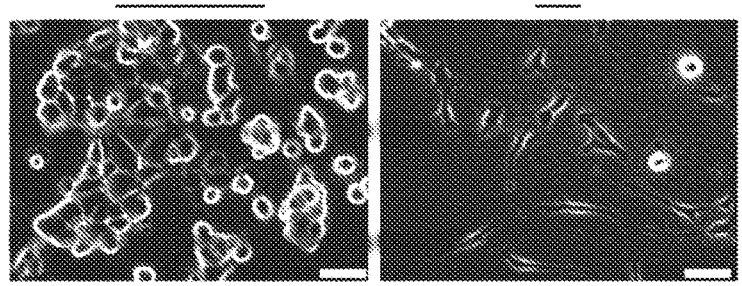
Figure 1:
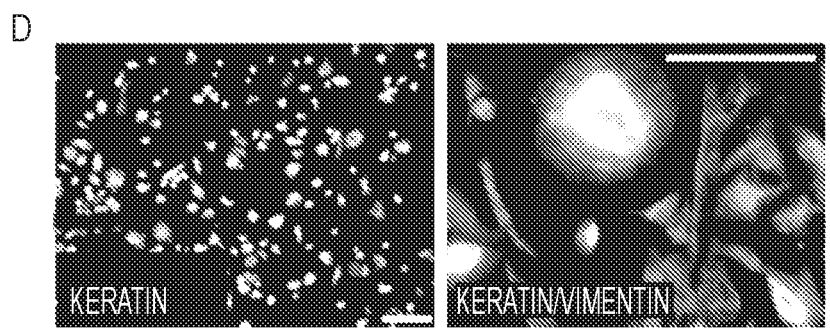
Figure 1:
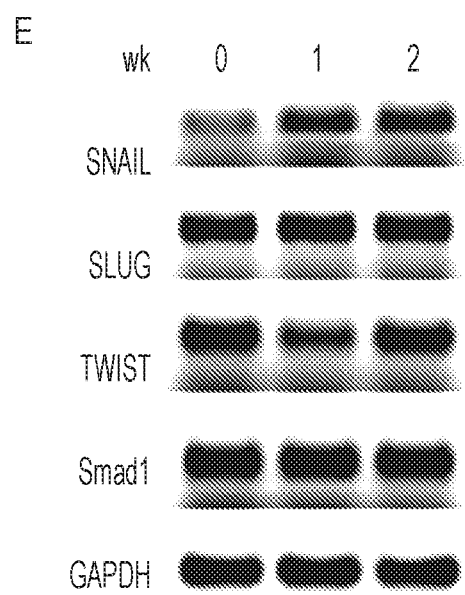
Figure 2:
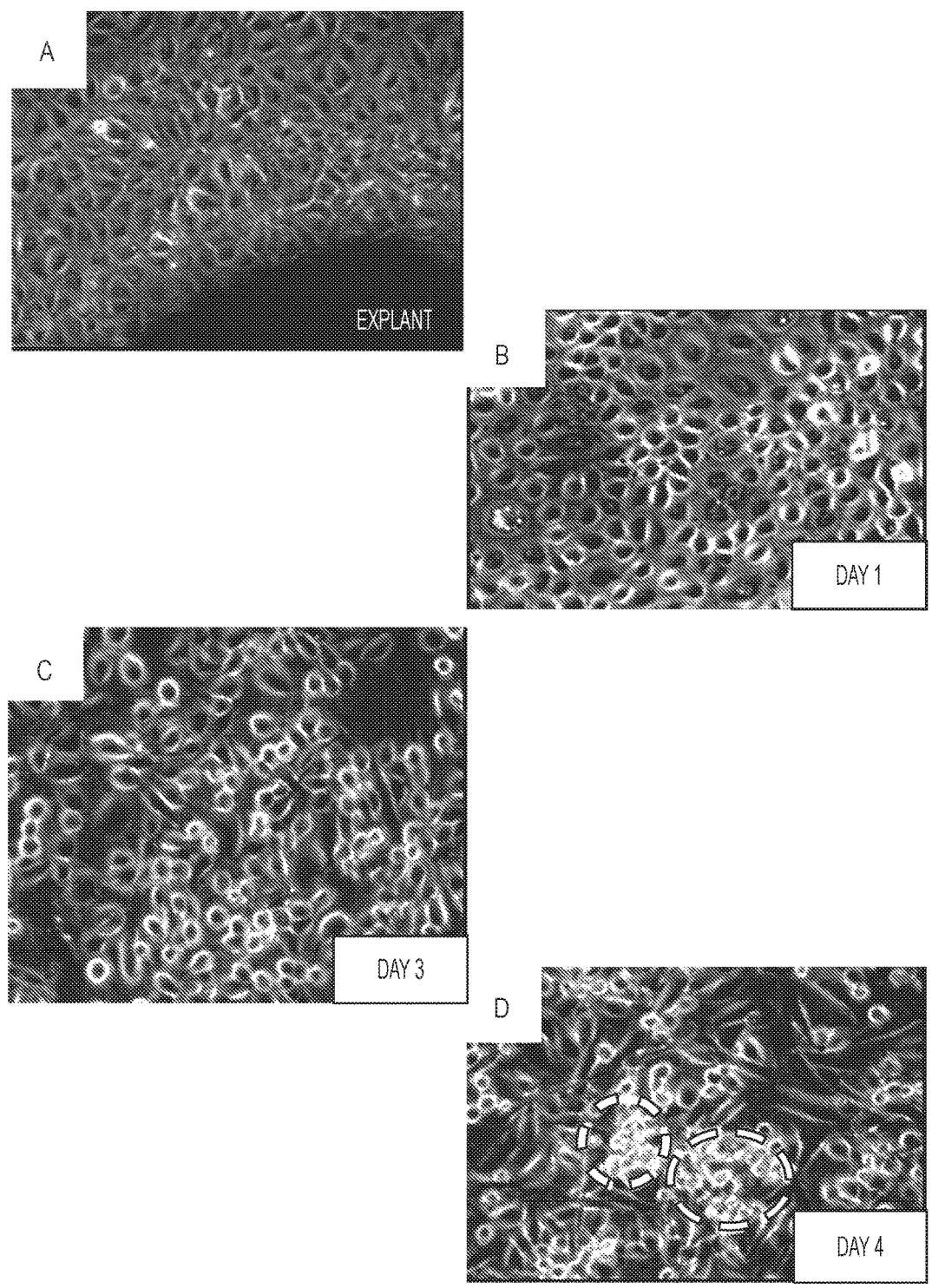

As described below, the present invention features compositions comprising an HGF/IgG complex and methods of using such compositions to reduce ischemic reperfusion injury.

The invention is based at least in part on the discovery that early treatment with HGF/IgG complexes after myocardial ischemia with reperfusion was able to rescue tissue by vasoprotection through c-Met and a receptor-like tyrosine kinase (RYK) signaling.

Vascular protection early after myocardial ischemia with reperfusion may reduce vascular injury and prevent impending infarct expansion. Epicardial cells support cardiac development, repair and remodeling after injury. It was hypothesized that secreted ligands from human epicardial derived cells would protect vascular integrity after myocardial ischemia with reperfusion. During simulated ischemia in culture (24-48 hours), concentrated human epicardial-derived cell-conditioned medium (EPI CdM) increased survival of primary cardiac endothelial cells. In a rat myocardial ischemia model, human epicardial-derived cell-conditioned medium treatment reduced vascular injury in vivo after reperfusion. By phospho-Receptor Tyrosine Kinase (RTK) arrays, ELISA, and neutralizing antibody screens Hepatocyte Growth Factor (HGF) was identified as a key vaso-protective factor in epicardial derived cell-conditioned medium. Unexpectedly, it was observed that ~30% of HGF in human epicardial-derived cell-conditioned medium formed complexes with polyclonal IgG. Following reperfusion, preparations of HGF/IgG complexes provided greater vascular protection than free HGF with IgG (i.e. non-complexed, matched dose). HGF/IgG complexes localized to blood vessels in vivo and increased retention time after administration. In subsequent screens, it was found that "related to tyrosine kinase" receptor (a.k.a. RYK) was phosphorylated after exposure of cardiac endothelial cells to HGF/IgG complexes, but not to free HGF with IgG. Notably, the added protection conferred by HGF/IgG complexes was lost after antibody blockade of receptor-like tyrosine kinase (RYK).

Accordingly, the invention provides methods and compositions using HGF/IgG complexes for vasoprotection and vascular integrity in myocardial ischemia after reperfusion. Furthermore the invention provides methods for treatment of subjects having or at risk of developing myocardial ischemia, cardiovascular disease or related disorders by administering or delivering HGF/IgG complexes or concentrated human epicardial-derived cell-conditioned medium containing HGF/IgG complexes in vivo.

Epicardial derived cells play important roles in development and repair and remodeling after cardiac injury, in part through paracrine activity. After myocardial ischemia, epicardial derived cells secrete factors that provide vascular protection and/or increase angiogenesis; these effects correlate with decreased infarct size and improved cardiac function after myocardial ischemia. Here HGF was identified as an abundant protective factor secreted by human epicardial-derived cells into conditioned medium (EPI CdM). Concentrated human epicardial-derived cells-conditioned medium was observed to protect cultured cardiac microvascular endothelial cells from hypoxic injury during simulated ischemia in an HGF-dependent manner. Furthermore, infusion of concentrated human epicardial-derived cells-conditioned medium prevented vascular leak and promoted microvascular cell survival when administered upon reperfusion after myocardial ischemia. Previous reports have demonstrated the benefits of "free" HGF in myocyte survival after myocardial ischemia and reperfusion, and its role in vascular protection after injury to other organs including the lung and brain. Notably, however, the present study showed that the ability of concentrated human epicardial-derived cells-conditioned medium to provide vascular protection was only partly due to its free HGF content.

Along with free HGF, concentrated human epicardial-derived cells conditioned medium was shown to contain HGF in a different form; this HGF existed in complexes containing IgG. Administration of HGF as prepared HGF/IgG complexes enhanced vascular protection mediated by HGF for cultured endothelial cells and also in vivo after ischemia with reperfusion. In further experiments, it was determined that enhanced vascular protection conferred by HGF/IgG complexes was due to phosphorylation of the receptor-like tyrosine kinase (RYK) receptor. Notably, free HGF treatment did not phosphorylate the receptor-like tyrosine kinase (RYK) receptor. These results indicate that by simultaneously signaling through c-Met and receptor-like tyrosine kinase (RYK), HGF/IgG complexes provide a valuable therapeutic that provides vascular protection after myocardial ischemia with reperfusion and perhaps other vascular injuries.

Therapeutic Methods

Compositions comprising HGF/IgG complexes are useful for preventing or ameliorating tissue damage associated with ischemic reperfusion injury (e.g., myocardial ischemic reperfusion injury). In one therapeutic approach, an isolated Hepatocyte Growth Factor (HGF)/IgG complex is administered systemically. The dosage of the administered isolated Hepatocyte Growth Factor (HGF)/IgG complex depends on a number of factors, including the size and health of the individual patient. For any particular subject, the specific dosage regimes should be adjusted over time according to the individual need and the professional judgment of the person administering or supervising the administration of the compositions.

Pharmaceutical Compositions

In one embodiment, a composition of the invention comprises or consists essentially of an isolated Hepatocyte Growth Factor (HGF)/IgG complex. An isolated Hepatocyte Growth Factor (HGF)/IgG complex can be conveniently provided to a subject as sterile liquid preparations, e.g., isotonic aqueous solutions, suspensions, emulsions, dispersions, or viscous compositions, which may be buffered to a selected pH. A composition comprising an isolated Hepatocyte Growth Factor (HGF)/IgG complex may be provided as liquid or viscous formulations. For some applications, liquid formations are desirable because they are convenient to administer, especially by injection. Where prolonged contact with a tissue is desired, a viscous composition may be preferred. Such compositions are formulated within the appropriate viscosity range. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions are prepared by mixing an isolated Hepatocyte Growth Factor (HGF)/IgG complex in the required amount of the appropriate solvent with various amounts of the other ingredients, as desired. Such compositions may be in admixture with a suitable carrier, diluent, or excipient, such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells or agents present in their conditioned media.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent, such as methylcellulose. Other suitable thickening agents include, for example, xanthan gum, carboxymethyl cellulose, hydroxypropyl cellulose, carbomer, and the like. The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form). Those skilled in the art will recognize that the components of the compositions should be selected to be chemically inert.

Compositions comprising an isolated Hepatocyte Growth Factor (HGF)/IgG complex are administered in an amount required to achieve a therapeutic or prophylactic effect. Such an amount will vary depending on the conditions. Typically, biologically active isolated Hepatocyte Growth Factor (HGF)/IgG complexes will be purified and subsequently concentrated so that the protein content of the composition is increased by at least about 5-fold, 10-fold or 20-fold over the amount of protein originally present in the media. In other embodiments, the protein content is increased by at least about 25-fold, 30-fold, 40-fold or even by 50-fold. Preferably, the composition comprises an effective amount of an isolated HGF/IgG complex.

The precise determination of what would be considered an effective dose is based on factors individual to each subject, including their size, age, sex, weight, and condition of the particular subject. Dosages can be readily ascertained by those skilled in the art from this disclosure and the knowledge in the art.

Optionally, the methods of the invention provide for the administration of a composition of the invention to a suitable animal model to identify the dosage of the composition(s), concentration of components therein and timing of administering the composition(s), which elicit vasoprotection, reduce vascular injury, or induce another desirable biological response. Such determinations do not require undue experimentation, but are routine and can be ascertained without undue experimentation Methods of Delivery Compositions comprising an isolated HGF/IgG complexes may be delivered to a subject in need thereof. Modes of administration include intramuscular, intra-cardiac, oral, rectal, topical, intraocular, buccal, intravaginal, intracisternal, intra-arterial, intracerebroventricular, intratracheal, nasal, transdermal, within/on implants, e.g., fibers such as collagen, osmotic pumps, or parenteral routes. The term "parenteral" includes subcutaneous, intravenous, intramuscular, intraperitoneal, intragonadal or infusion.

The compositions can be administered via localized injection, including catheter administration, systemic injection, localized injection, intravenous injection, or parenteral administration. When administering a therapeutic composition of the present invention, it will generally be formulated in a unit dosage injectable form (solution, suspension, emulsion). Dosages can be readily adjusted by those skilled in the art (e.g., a decrease in purity may require an increase in dosage). Compositions of the invention can be introduced by injection, catheter, or the like. Compositions of the invention include pharmaceutical compositions comprising cellular factors of the invention and a pharmaceutically acceptable carrier. Administration can be autologous or heterologous.

Methods for Evaluating Therapeutic Efficacy

In one approach, the efficacy of the treatment is evaluated by measuring, for example, vascular integrity. Such methods are standard in the art and are described herein. In particular, a method of the present invention, decreases vascular permeability by at least about 5%, 10%, 20%, 40%, 50%, 60%, 70%, 80%, 90%, 100%. In one embodiment, therapeutic efficacy is assessed by measuring a reduction in apoptosis. Apoptotic cells are characterized by characteristic morphological changes, including chromatin condensation, cell shrinkage and membrane blebbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Assays for apoptosis are known in the art. Exemplary assays include TUNEL (Terminal deoxynucleotidyl Transferase Biotin-dUTP Nick End Labeling) assays, caspase activity (specifically caspase-3) assays, and assays for fas-ligand and annexin V. Commercially available products for detecting apoptosis include, for example, Apo-ONE® Homogeneous Caspase-3/7 Assay, FragEL TUNEL kit (ONCOGENE RESEARCH PRODUCTS, San Diego, Calif.), the ApoBrdU DNA Fragmentation Assay (BIOVISION, Mountain View, Calif.), and the Quick Apoptotic DNA Ladder Detection Kit (BIOVISION, Mountain View, Calif.).

Kits

The invention provides kits for the treatment or prevention of vascular reperfusion injury, after myocardial ischemia (MI) and the treatment of diseases or disorders associated with myocardial ischemia (e.g. ischemic injuries, myocardial infarction and cardiovascular disease). In one embodiment, the kit includes a therapeutic or prophylactic composition containing an effective amount of medium (e.g. concentrated human epicardial derived cell-conditioned medium) that expresses HGF/IgG complexes in unit dosage form. In some embodiments, the kit comprises a sterile container which contains a therapeutic or prophylactic composition of medium; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired medium of the invention is provided together with instructions for administering the medium to a subject having or at risk of developing myocardial ischemia, ischemic injury or myocardial infarction or in need of reperfusion after myocardial ischemia. The instructions will generally include information about the use of the composition for the treatment or prevention of myocardial ischemia (e.g., ischemic injury, myocardial infarction or vascular injury after reperfusion). In other embodiments, the instructions include at least one of the following: description of the medium; dosage schedule and administration for treatment or prevention of myocardial ischemia (e.g., myocardial infarction, vascular injury after reperfusion, cardiovascular disease) or symptoms thereof; precautions; warnings; indications; counter-indications; over dosage information; adverse reactions; animal pharmacology; clinical studies; and/or references, the treatment regime, reagents, equipment (test tubes, reaction vessels, needles, syringes, etc.) and standards for calibrating or conducting the treatment. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Isolation of Adult Human Epicardial Progenitor Cells and Cells Undergoing Epithelial to Mesenchymal Transformation into Precursor Cells The epicardial layer from adult human right atrial heart tissue is a single layer of epithelial cells that stained positive for keratin (epithelial intermediate filament protein, FIG. 1A). Human epicardial cells were isolated from right atrial appendages commonly removed to place a cardiopulmonary bypass cannula as part of cardiac surgery. The cells were successfully isolated from 12 out of 13 donors (Table 1, below).

TABLE 1

Patient Data for Epicardial Progenitor Cell Isolations.

| Sex | Age | HTN | DM | CAD | MR | AS | LVEF |
|---|---|---|---|---|---|---|---|
| M | 47 | + | + | + | − | − | 0.45 |
| M | 59 | + | − | + | − | − | NI |
| M | 57 | − | − | + | − | − | NI |

TABLE 1-continued

Patient Data for Epicardial Progenitor Cell Isolations.

| Sex | Age | HTN | DM | CAD | MR | AS | LVEF |
|---|---|---|---|---|---|---|---|
| M | 52 | − | − | − | + | − | NI |
| M | 57 | − | − | + | − | − | NI |
| F | 53 | + | − | + | − | − | NI |
| M | 80 | + | − | − | − | + | NI |
| F | 72 | + | − | − | + | − | 0.45 |
| M | 53 | + | + | + | − | − | NI |
| M | 78 | − | − | + | − | − | NI |
| F | 72 | + | − | + | − | − | NI |
| F | 60 | + | − | + | − | − | NI |

Abbreviations:
HTN, hypertension;
DM, diabetes mellitus;
CAD, coronary artery disease;
MR, mitral regurgitation;
AS, aortic stenosis;
LVEF, left ventricular ejection fraction.

Figure 3:
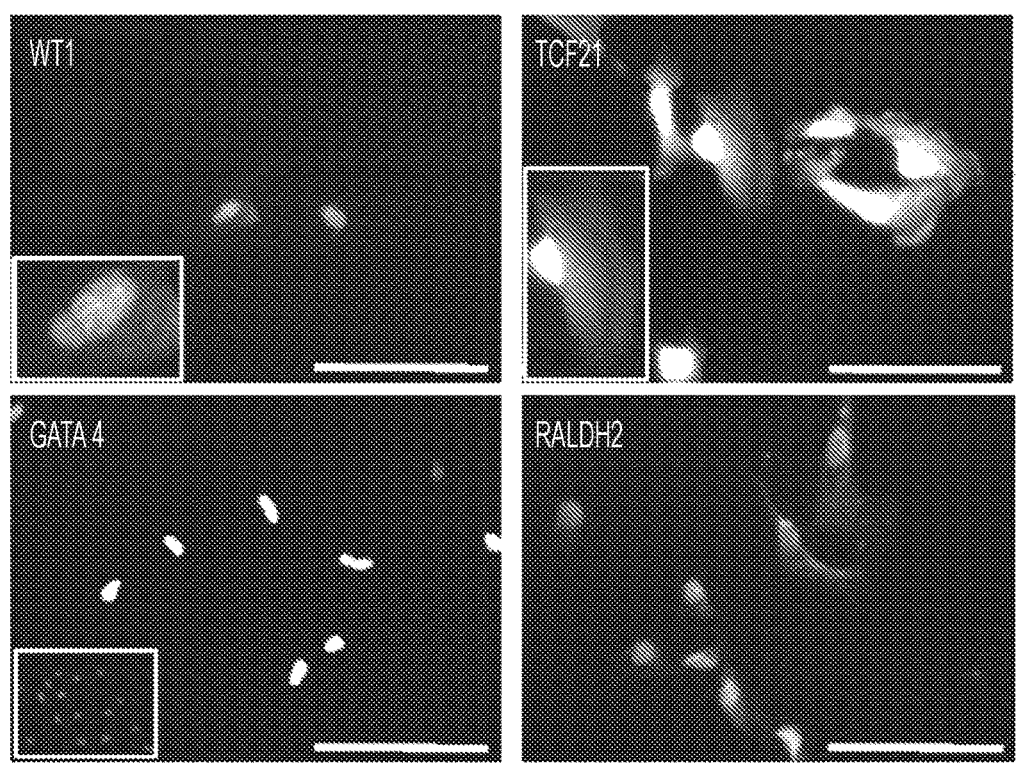
Figure 3:
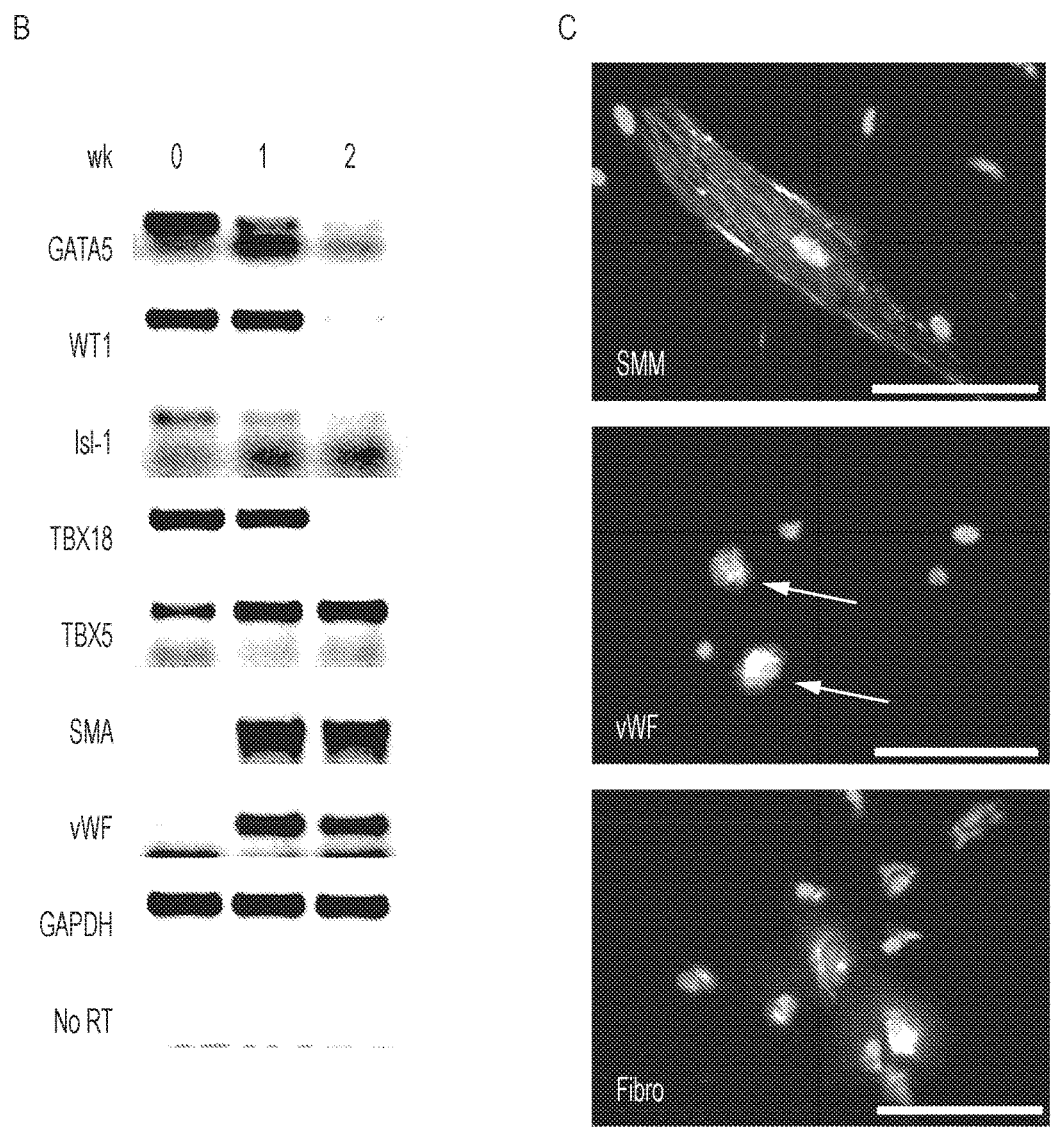
Figure 4:
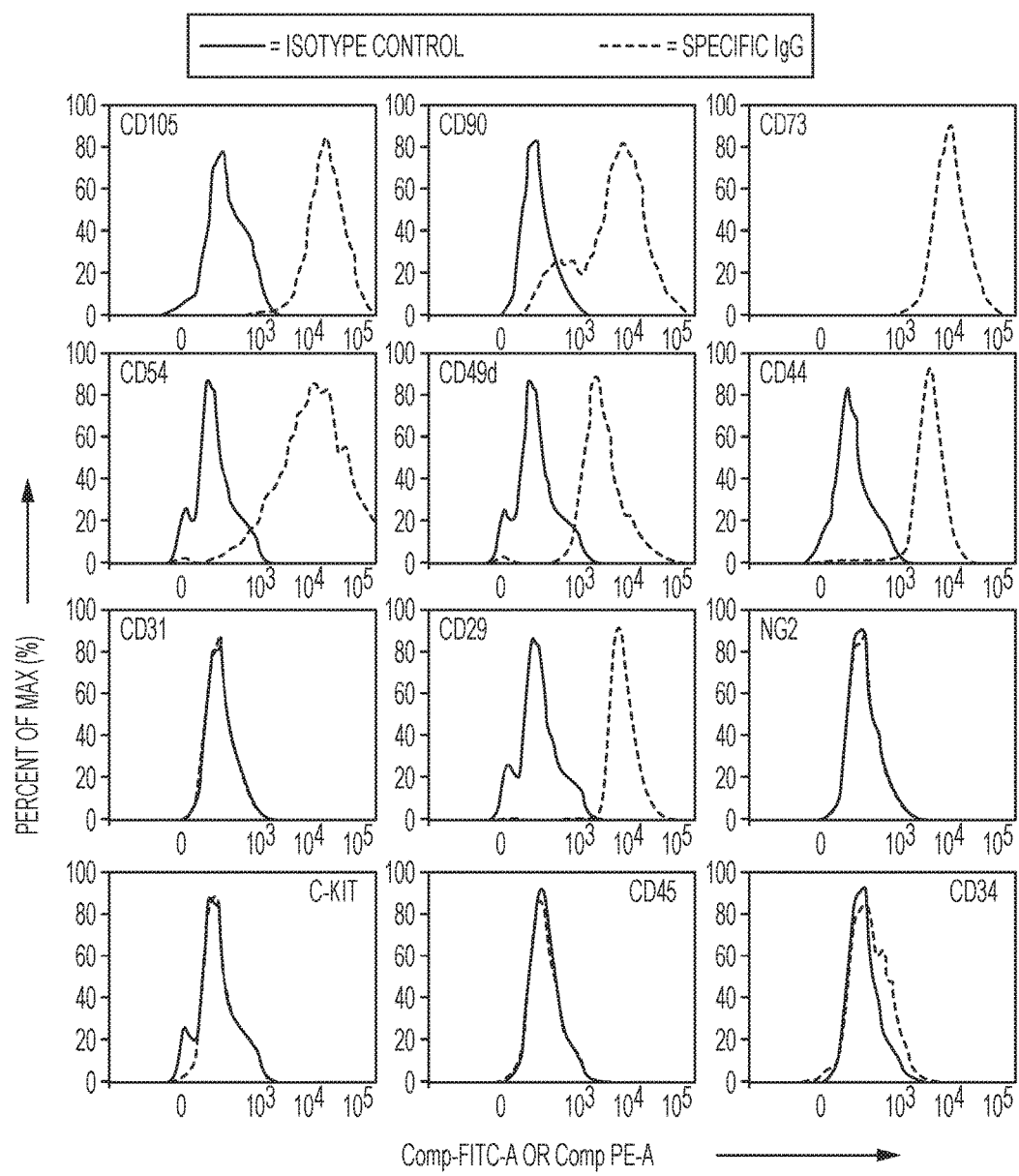
FIG. 4 shows the cell surface phenotype of human epicardial derived cells after epithelial to mesenchymal transformation. Many of the cells were positive for markers associated with human bone marrow-derived mesenchymal stem cells: CD105, CD90, CD73, CD54, CD49d, CD44, and CD29. Note that the expanding cell population was negative for CD45, CD34, and CD31 as well as c-kit and NG2. The green line represents the signal from cells stained with isotype control antisera and the red line represents the signal from cells from the same culture stained with specific antisera.

Two different methods were developed to isolate proliferating epicardial progenitor cells from right atrial appendages. In the first method, explant cultures were generated from minced right atrial appendage (FIG. 1B). Once fibroblast outgrowth reached about 70% confluence, the medium was switched to a low serum stem/progenitor cell growth medium containing Leukemia inhibitory factor (LIF), Epidermal growth factor (EGF), and basic fibroblast growth factor (bFGF). Under these conditions, floating spheroids and bunches of cells formed and were collected, placed into new culture dishes and expanded (FIG. 1C). In the second method, epicardial tissue was carefully dissected from the surfaces of human right atrial appendages and cultured directly (FIGS. 2A-2D). The epicardial progenitor cells had an epithelial morphology and expressed keratins (FIG. 1D). Differentiation via epithelial to mesenchymal transformation of the epicardial progenitor cells into a mixture of transitory-amplifying precursor cells was induced by culture in medium containing 10% fetal calf serum (FIG. 1D). During epithelial mesenchymal transition into precursor cells, the progenitor cells down regulated their expression of keratins and expressed vimentin (FIG. 1D). By RT-PCR, several mRNAs for markers of epithelial mesenchymal transition: Snail, Slug, Twist and Smad1 were detected (FIG. 1E). In addition, the human precursor cells expressed transcription factors reported to be expressed by murine epicardial cells: Wilms tumor protein 1 (WT1), retinaldehyde dehydrogenase 2 (RALDH2), GATA4, transcription factor 21 (TCF21) (FIG. 3A). Expression of mRNA for several epicardial-related transcription factors decreased as the cells differentiated (see GATA5, WT1, ISLET1 (Isl-1), and T-box transcription factor 18 (Tbx18); FIG. 3B). In contrast, expression of mRNA for smooth muscle actin and von Willebrand Factor (vWF) increased (FIG. 3B), indicating that some human epicardial derived cells might be differentiating into vascular smooth muscle cells or myofibroblasts and others into endothelial cells, respectively. At 2 weeks after epithelial mesenchymal transition, by immunocytochemistry, a few cells that were positive for smooth muscle myosin and others for von Willebrand Factor were detected, confirming that some of the cells were precursors of smooth muscle cells and endothelial cells (FIG. 3C). Notably, however, the majority of epicardial-derived cells were positive for prolyl-4-hydroxylase, an enzyme involved in collagen biosynthesis and a marker of fibroblasts. Cell surface phenotyping demonstrated that the human epicardial derived cells were negative for hematopoietic and endothelial cell surface markers such as CD31, CD34, CD45, and c-kit, and also the vascular pericyte marker NG2. Multiple cell surface antigens typical of bone marrow mesenchymal stem cells, such as CD105, CD90, CD73, CD54, CD49d, CD44, and CD29 were expressed by human epicardial derived cells (FIG. 4). As a second method, a slightly faster protocol was developed to isolate human epicardial derived cells by direct culture of human epicardium dissected from the surface of right atrial appendages. Immunocytochemistry, cell surface phenotyping, and ELISA data indicated that the precursor cells derived from epithelial to mesenchymal transformation did not differ whether the cells were rapidly induced to undergo epithelial to mesenchymal transformation or were maintained for several weeks as epithelial progenitor cells and then induced to undergo epithelial to mesenchymal transformation.

Figure 5:
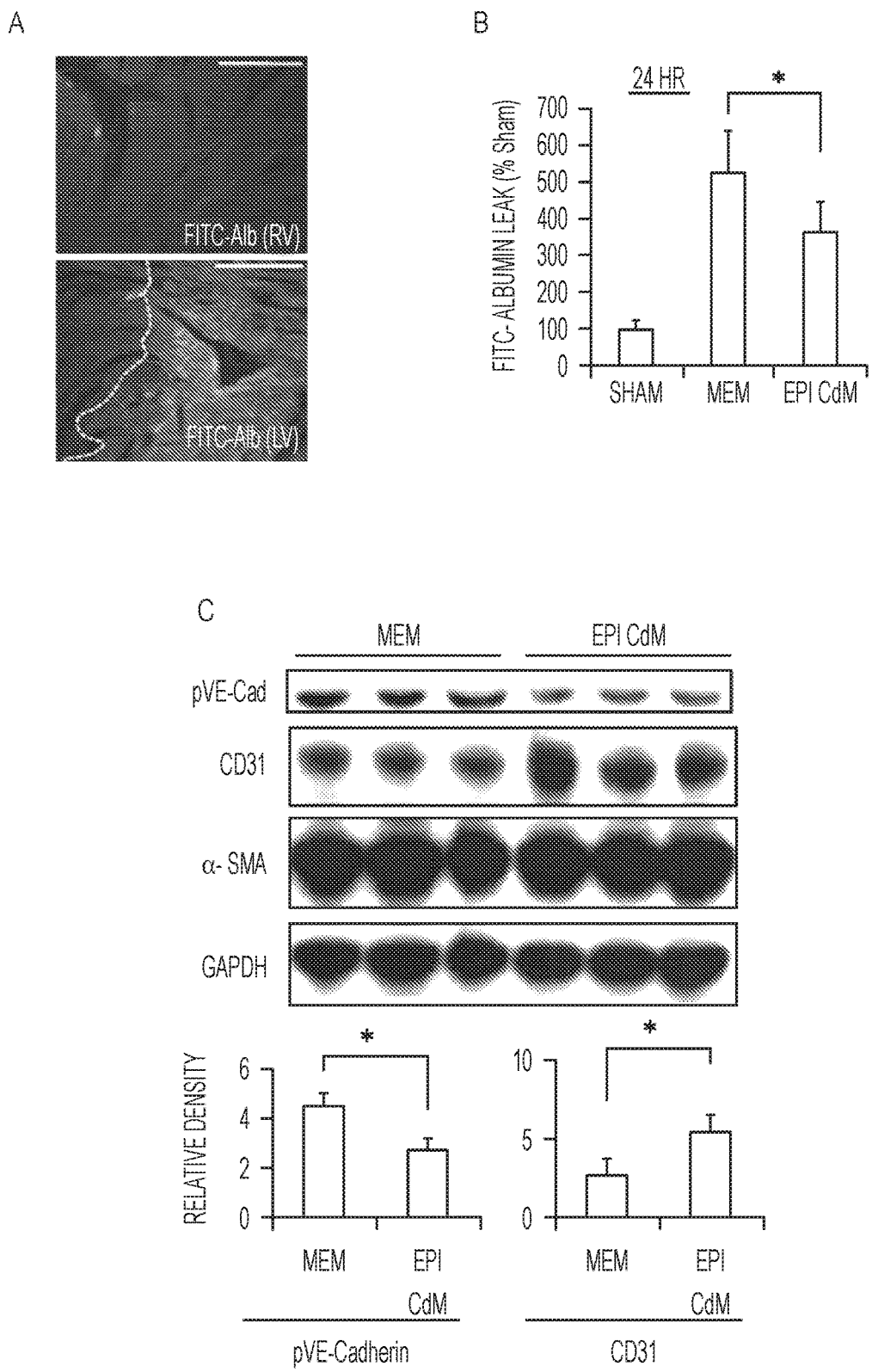
FIGS. 5A-5C show that human epicardial-derived cell-conditioned medium treatment improved vascular integrity after myocardial ischemia with reperfusion in rats.
Figure 7:
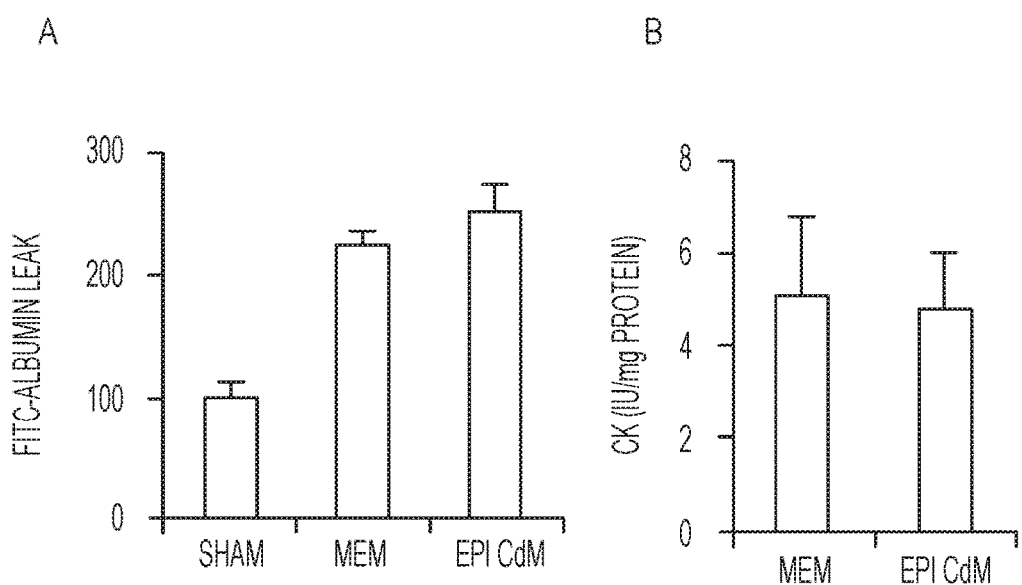
FIGS. 7A and 7B show that a single, injected dose of human epicardial-derived cell-conditioned medium did not protect against vascular leak at 72 hours after myocardial ischemia and treatment.

Example 2: Human Epicardial-Derived Cells Conditioned Medium Treatment Promoted Vascular Integrity In Vivo To determine whether human epicardial-derived cell-conditioned medium (EPI CdM) could provide vascular protection in vivo, adult male Fischer rats underwent 2 hours of transient ischemia followed by 24 hours of reperfusion. They were then treated with either MEM (vehicle control) or human epicardial-derived cell-conditioned medium at the time of reperfusion. Twenty-four hours after ischemia/reperfusion the amount of FITC extravasation was quantified in each treated animal by normalizing it to the level of extravasation in sham-operated animals. On histological examination, a greater level of FITC-albumin extravasation was observed from vessels in the infarcted region from the left ventricle (LV) when compared with no leak from intact vessels outside the region of infarction, including the right ventricle (RV) (FIG. 5A). Heart homogenates from MEM-treated rats had 37.8% greater FITC fluorescence than homogenates from rats treated with human epicardial-derived cell-conditioned medium. The amount of extravasated FITC-albumin in the MEM-treated group was 527.4%±109.33 of sham, whereas in the human epicardial-derived cell-conditioned medium (EPI CdM)-treated group it was 359.7%±78.82 of sham ($p \leq 0.05$, n=5 per group; FIG. 5B). In contrast to the observed treatment effect at 24 hours after reperfusion, at 72 hours after human epicardial-derived cell-conditioned medium injection there was no longer a significant difference between human epicardial derived cell-conditioned medium-treated and MEM-treated rats (p=0.08; FIG. 7A). These data indicated that further vascular protection might be obtained upon repeated doses of human epicardial-derived cell-conditioned medium over several days.

Following myocardial ischemia, the loss of myocardial creatine kinase (CK) activity directly reflects the loss of viable myocardium after myocardial ischemia. To determine the effect of human epicardial-derived cell-conditioned medium on myocytes at 24 hours after ischemia-reperfusion, an enzymatic assay was performed to quantify CK activity in the left ventricle (as previously described). At 24 hours after myocardial ischemia, no difference in the amount of residual CK activity was observed in the left ventricles of animals treated with MEM or human epicardial-derived cell-conditioned medium (MEM, 5.04±1.78 IU/mg of protein, human epicardial-derived cell-conditioned medium, 4.72±1.26 IU/mg of protein, p=0.74) (FIG. 7B). Thus, human epicardial-derived cells-conditioned medium-mediated effects on cardiac myocyte survival were not detectable early after reperfusion injury and treatment.

VE-Cadherin is a key junctional protein involved in maintenance of endothelial barrier integrity. The level of phosphorylated VE-Cadherin (pVE-Cadherin) is a useful marker for increased vascular permeability. To investigate vascular effects of human epicardial-derived cell-conditioned medium treatment, immunoblotting was performed on the soluble fraction from left ventricular homogenates. At 24 hours after myocardial ischemia, reperfusion, and treatment, the level of pVE-Cadherin (pY658) was significantly higher in the MEM-treated group of animals than in the human epicardial-derived cell-conditioned medium-treated group ($p \leq 0.01$, n=3; FIG. 5C). To examine the relative effects of human epicardial-derived cell-conditioned medium treatment on vascular endothelial cells and smooth muscle cells, next the levels of CD31 (PECAM1, endothelial marker) and alpha smooth muscle actin (α-SMA) were compared in left ventricle homogenates from the MEM and human epicardial-derived cell-conditioned medium treatment groups. Consistent with enhanced endothelial cell survival, significantly higher levels of CD31 were observed in animals treated with human epicardial-derived cell-conditioned medium compared with MEM-treated controls ($p \leq 0.05$, n=3; FIG. 5C). In contrast to the CD31 results, equal amounts of soluble alpha smooth muscle actin (α-SMA) for the MEM and human epicardial-derived cell-conditioned medium treatment groups were observed (FIG. 5C). Together with the data for CK activity, these data indicated that endothelial cells were the principal target of human epicardial-derived cell-conditioned medium treatment early after reperfusion.

Figure 8:
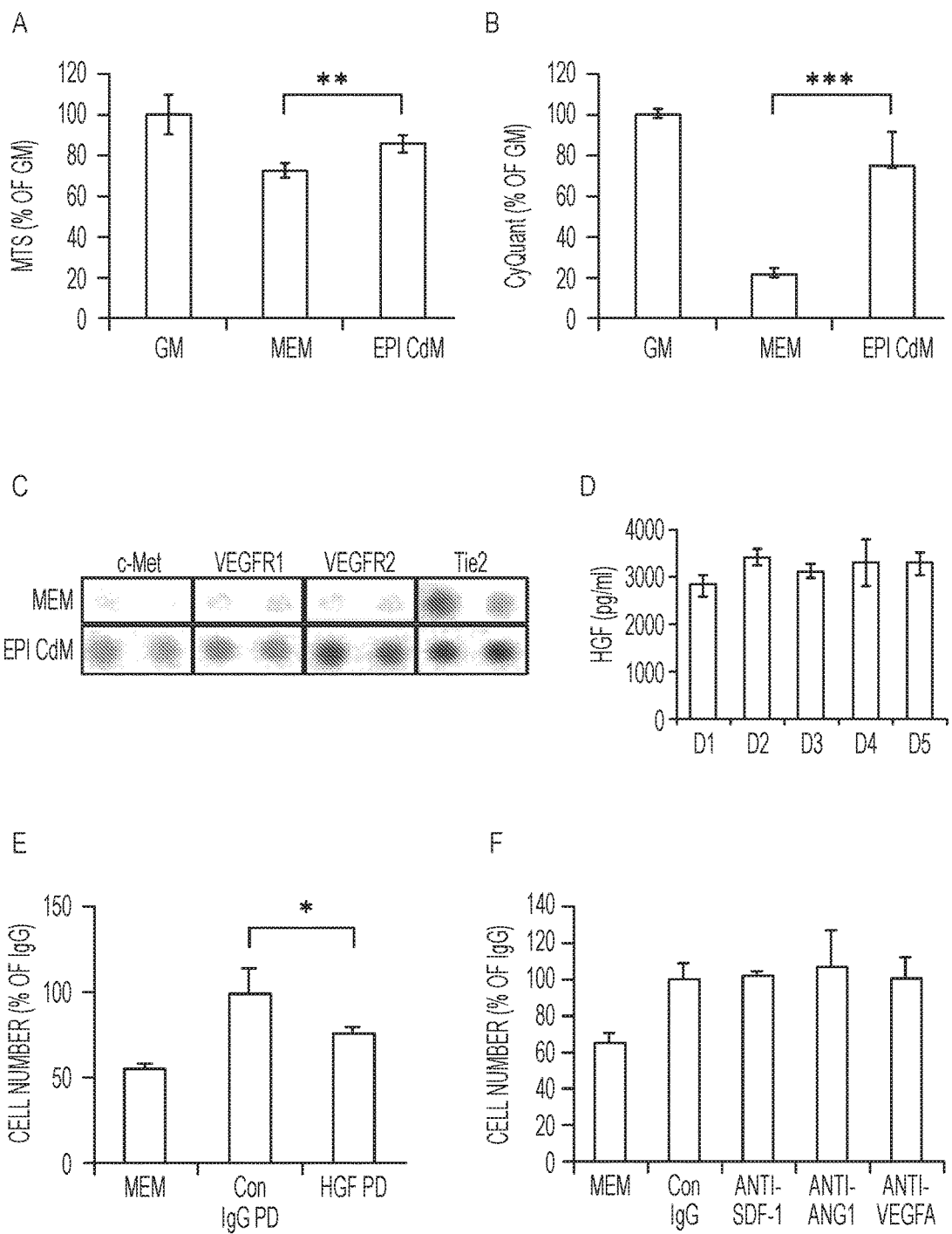
FIGS. 8A-8F show that Hepatocyte Growth Factor (HGF) was a key vaso-protective factor in human epicardial-derived cell-conditioned medium.

Example 3: Human Epicardial-Derived Cell-Conditioned Medium Protected Human Cardiac Endothelial Cells During Simulated Ischemia Human cardiac endothelial cells were purchased at passage 1 from Lonza (Catalog # CC-2585 and CC-7030). To further investigate human epicardial-derived cell-conditioned medium-mediated protection (EPI CdM) of cardiac endothelial cells, cell protection assays were performed under conditions of simulated ischemia (low glucose medium, 1% oxygen, for 24 or 48 hours). Compared with incubation in MEM (vehicle control), human epicardial-derived cell-conditioned medium generated from human epicardial derived cells of donors from 52 to 80 years of age all protected primary human cardiac endothelial cells from simulated ischemic injury for 24 hours (FIG. 8A). Human epicardial-derived cell-conditioned medium concentrated to 10-fold provided a greater level of cell protection than did unconcentrated (1×) human epicardial-derived cells conditioned medium. The 10× human epicardial-derived cell-conditioned medium protected human coronary artery endothelial cells and microvascular endothelial cells for 48 hours (FIG. 8B).

Figure 6:
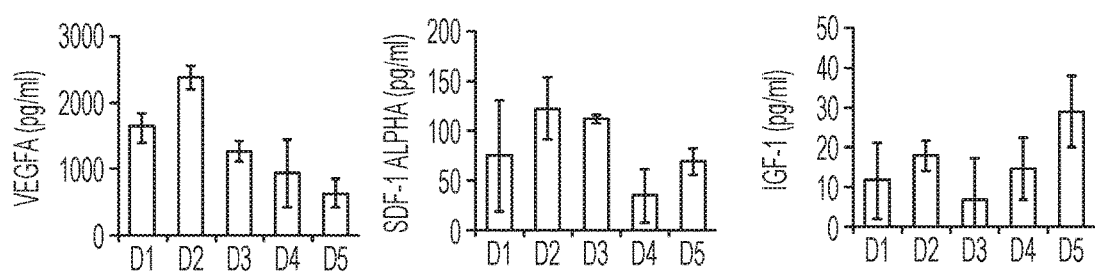
FIG. 6 depicts three graphs showing additional data for proteins secreted by human epicardial derived cells. ELISA data for vascular endothelial growth factor A (VEGFA) and stromal cell-derived factor 1 alpha (SDF-1 α). Data are shown for 5 different human donors that range in age (52-80 years).

Example 4: HGF is a Key Vascular Protective Component of Human Epicardial-Derived Cell-Conditioned Medium To identify signaling pathways stimulated in cardiac endothelial cells following exposure to human epicardial-derived cell-conditioned medium (EPI CdM), phospho-receptor tyrosine kinase arrays were performed with lysates from human coronary artery endothelial cells previously exposed to MEM or 1× human epicardial-derived cell-conditioned medium. c-Met, vascular endothelial growth factor receptor 1 (VEGFR1), vascular endothelial growth factor receptor 2 (VEGFR2), fibroblast growth factor receptor 1 (FGFR1) and Tie1 (angiopoietin-1 receptor) were phosphorylated after human epicardial-derived cell-conditioned medium exposure and appeared to be increased relative to signals from the control array (MEM) (FIG. 8C). By ELISA, unconcentrated (1×) human epicardial-derived cell-conditioned medium from several different human donors contained HGF (about 3 ng/ml) (FIG. 8D), angiopoietin-1 (ANG1, between 446 pg/ml and 1.1 ng/ml), vascular endothelial growth factor A (VEGFA, between 500 pg/ml and 2.5 ng/ml), and stromal cell-derived factor 1-alpha (SDF-1 α, <150 pg/ml) (FIGS. 6 and 8D). Although fibroblast growth factor receptor 1 (FGFR1) phosphorylation by phospho-receptor tyrosine kinase array was observed, fibroblast growth factor 2 (FGF2) or fibroblast growth factor 9 (FGF9) was not detected in human epicardial-derived cell-conditioned medium by ELISA.

To examine the relative role of HGF and other angiogenic factors in protection conferred by human epicardial-derived cell-conditioned medium, pull-down assays were performed with growth factor-specific antisera. Compared with non-specific pull down (PD), HGF pull-down significantly reduced the protective effects of human epicardial-derived cell-conditioned medium (FIG. 8E). Importantly, pull-down of the other angiogenic factors from human epicardial-derived cell-conditioned medium did not decrease its protective effect (FIG. 8F).

Figure 9:
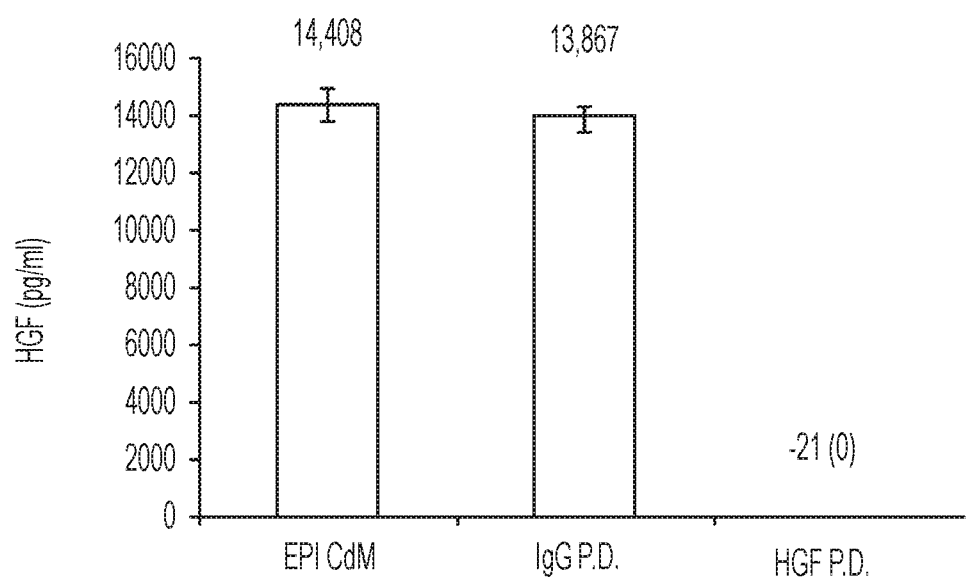
FIG. 9 shows a graph depicting a pull down of HGF from human epicardial-derived cell-conditioned medium. Using HGF specific antibody, HGF could be completely depleted from human epicardial-derived cell-conditioned medium as measured by ELISA.
Figure 11:
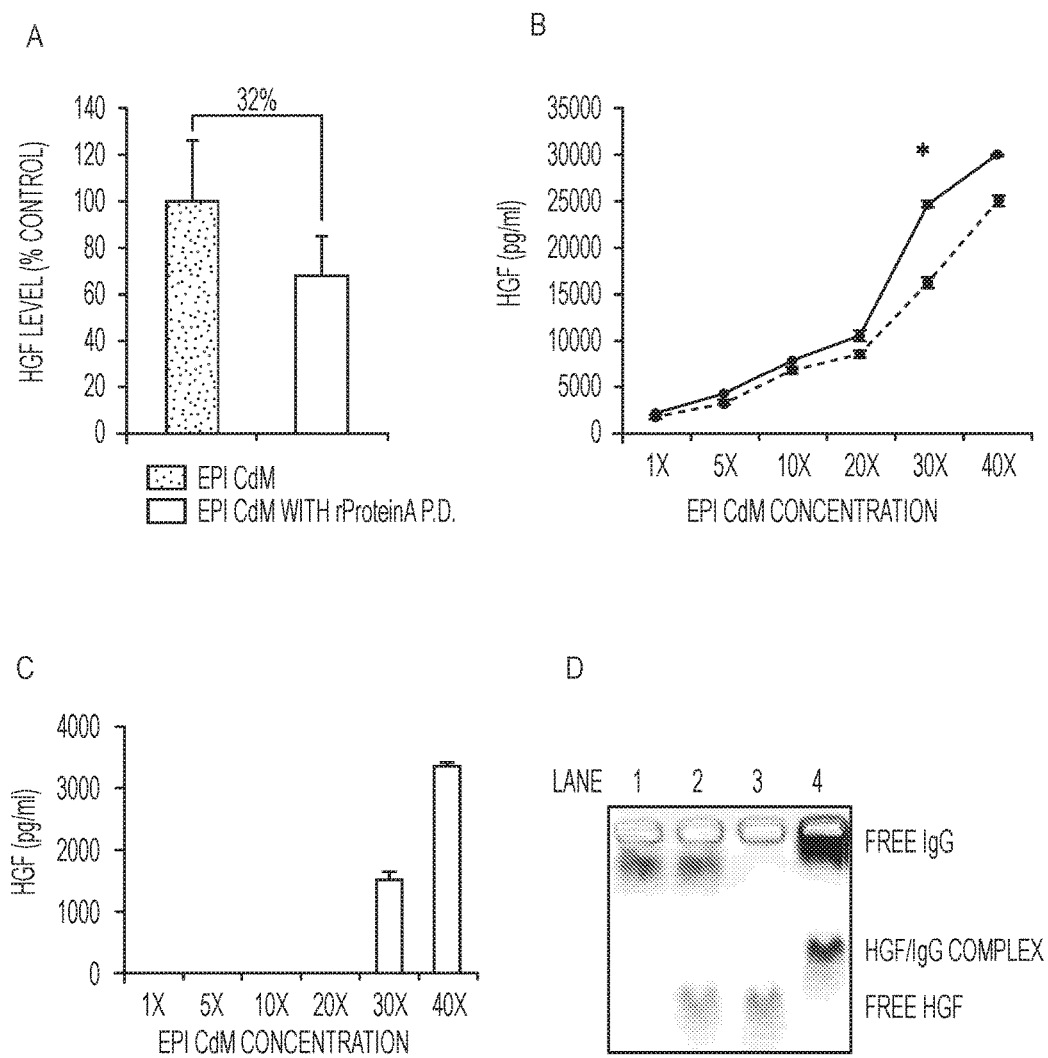
FIGS. 11A-11D show that concentrated human epicardial-derived cell-conditioned medium contained HGF/IgG protein complexes.

Example 5: Protein Complexes Containing HGF and IgG are Present in Concentrated Human Epicardial-Derived Cell-Conditioned Medium In experiments designed to neutralize HGF in 30× human epicardial-derived cell-conditioned medium (EPI CdM) using protein A Sepharose, an unexpected decrease in the HGF concentration of human epicardial-derived cell-conditioned medium was observed when it was incubated with non-specific polyclonal IgG alone (typically used as a control for specific IgG) (FIG. 9). The presence of left-over serum carrier proteins has been described in Conditioned Medium preparations, due to dynamic recycling of extracellular proteins by cellular vesicles. To determine whether HGF interacted with IgG from serum in human epicardial-derived cell-conditioned medium, 30× human epicardial-derived cell-conditioned medium was incubated with protein A Sepharose beads alone overnight and HGF levels were measured before and after bead incubation. A 32% decrease in HGF concentration was observed in human epicardial-derived cell-conditioned medium following the removal of the beads (FIG. 11A). These data indicate that HGF and IgG associated and formed complexes in human epicardial-derived cell-conditioned medium as a consequence of concentrating it ex vivo. To test this idea, human epicardial-derived cell-conditioned medium was first concentrated to varying degrees (1× to 40×). To determine if IgG was interacting with HGF a standard amount of IgG (non-specific polyclonal IgG, 2 ug/ml) was added to the series of human epicardial-derived cell-conditioned medium concentrations (to use as bait for HGF) and pull-downs were performed with Protein A Sepharose. As expected, increasing amounts of HGF were detected by ELISA when unmodified human epicardial-derived cell-conditioned medium was concentrated from 1× to 40×. Hypothetically, in the instance that IgG and HGF were interacting, a reduction in HGF level would be observed by ELISA. In support of this hypothesis, after pull-down, as human epicardial-derived cell-conditioned medium concentration increased, a concentration-dependent loss of HGF from human epicardial-derived cell-conditioned medium was observed; this loss was most significant for 30× human epicardial-derived cell-conditioned medium (p<0.05, FIG. 11B).

To confirm the co-precipitation of HGF with IgG from human epicardial-derived cell-conditioned medium, the beads were thoroughly washed after pull-down and then incubated in sodium deoxycholate. An ELISA on the deoxycholate-soluble fraction was performed to determine if HGF could be recovered from the beads. Increasing levels of HGF were detected after pull-down with IgG, corresponding to increasing human epicardial-derived cell-conditioned medium concentration. About 1.5 ng/ml HGF were detected from beads with 30× Conditioned Medium and about 2.8 ng/ml from beads with 40× Conditioned Medium (FIG. 11C). Although some interaction may have been present, at human epicardial-derived cell-conditioned medium concentrations lower than 30× Conditioned Medium, HGF could not be detected from beads by ELISA.

Having observed that HGF and IgG formed complexes as a consequence of increasing human epicardial-derived cell-conditioned medium concentration, it was investigated whether other angio genic factors in Conditioned Medium were also capable of interacting with IgG. A solid phase binding assay was performed to test the binding of purified growth factors (all obtained from R&D Systems) and non-specific IgG, incubated at the concentration where HGF and IgG had interacted maximally. To perform a quantitative measurement, high protein-binding plates were first coated with polyclonal non-specific capture IgG. At fixed concentrations of capture IgG, binding of an array of different angiogenic factors and growth factors was tested: HGF, angiopoietin 1 (ANG1), vascular endothelial growth factor (VEGF), insulin-like growth factor-1 (IGF-1), platelet-derived growth factor (PDGF), placenta growth factor (PLGF) and nerve growth factor (NGF). After washes, incubation in biotin-conjugated specific detection antibodies for each growth factor was used to measure the amount of factor bound to IgG. Only HGF was observed to bind the captured IgG with an affinity indicative of interaction (FIG. 11D). For all other factors, no signals from the plates were detected. For an additional control experiment HGF was incubated with bovine serum albumin (BSA); this is typically used as a non-specific carrier protein. HGF did not exhibit affinity for BSA.

Example 6: HGF/IgG Complexes Provide Enhanced Vascular Protection by Activating a Receptor-Like Tyrosine Kinase (RYK)

Figure 10:
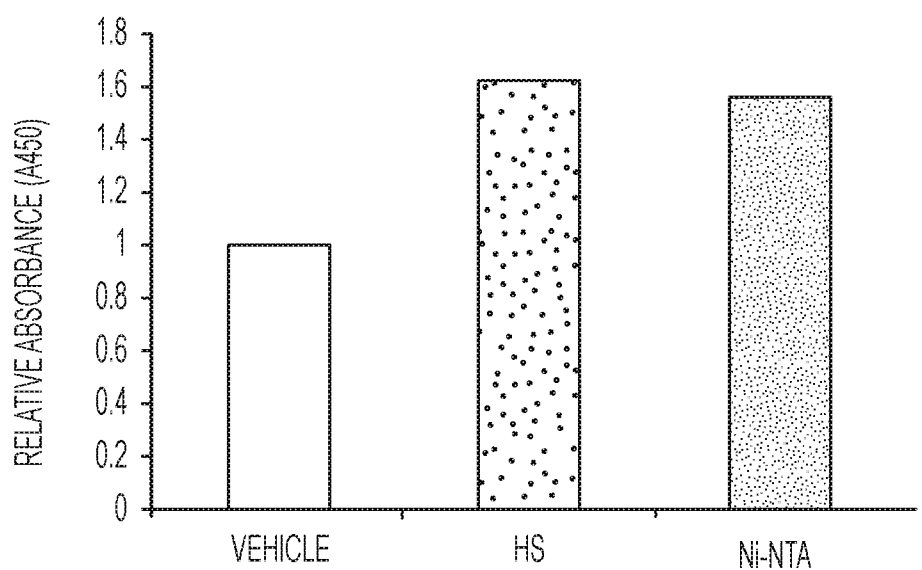
FIG. 10 is a graph showing absorbance as a measure of relative c-Met phosphorylation in response to recombinant HGF expressed by HEK293 cell in culture. HGF was expressed by HEK293 cells in culture with 5% serum. Media obtained from these cells was run over Heparin-sepharose column (HS) or Ni-NTA column for purification of His-tagged proteins. Cultured human epithelial cells were incubated 1 hour in vehicle or material eluted from Heparin-sepharose column (HS) and a column for gravity-flow purification of His-tagged proteins (Ni-NTA column, where the Ni-NTA material diluted 5-fold) and then lysed for ELISA. Absorbance is a measure of relative c-Met phosphorylation.
Figure 12:
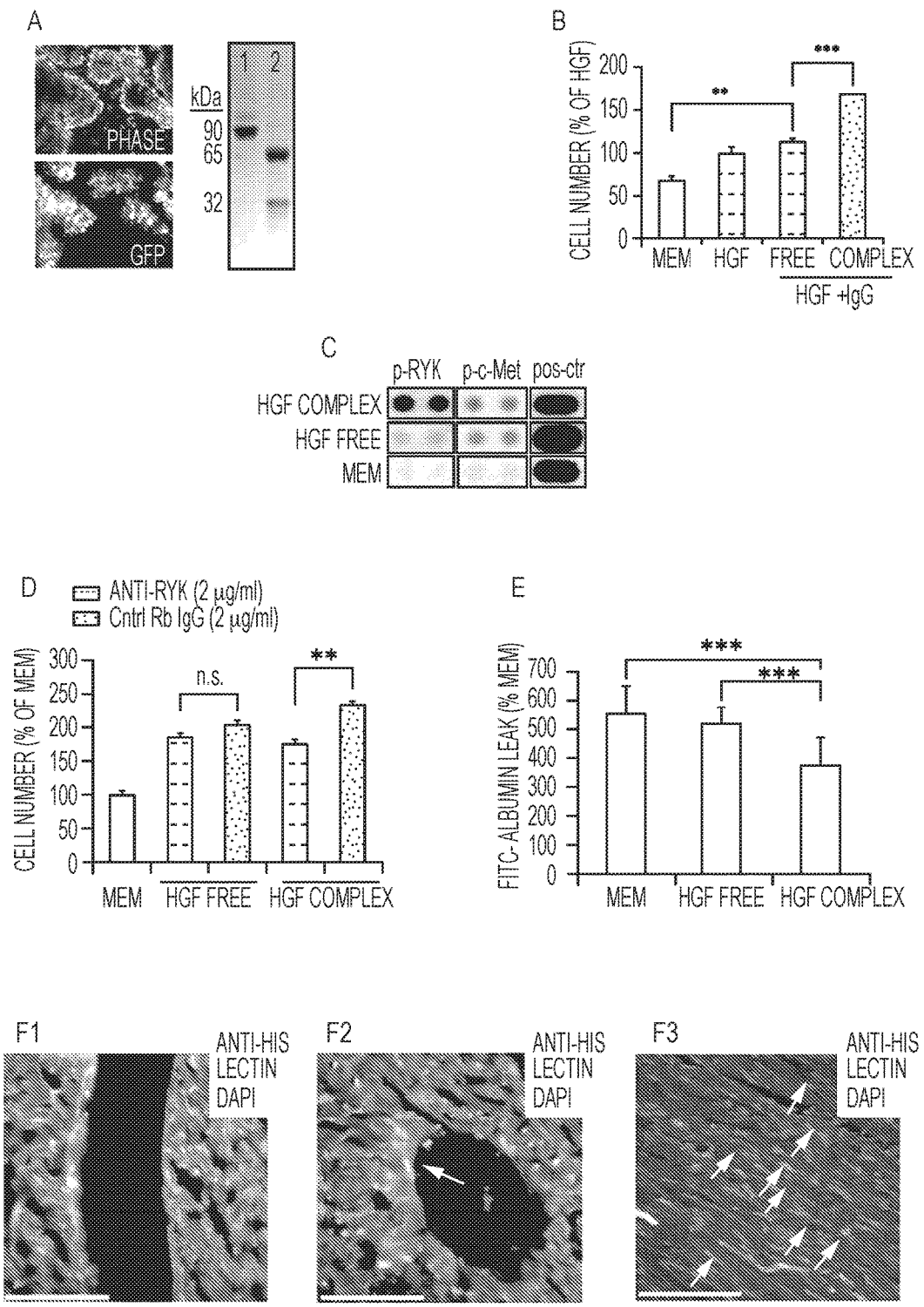
FIGS. 12A-12F show that HGF/IgG complexes enhanced vascular protection by interacting with a receptor-like tyrosine kinase (RYK).

As the above protein interactions were observed in vitro, it was interesting to learn if they had any physiological benefit(s). To investigate whether HGF/IgG complexes might protect vascular endothelial cells differently during tissue injury than would free HGF, ex vivo cell protection assays were performed under conditions designed to simulate ischemia (1% oxygen combined with nutrient deprivation). To ensure reproducibility across experiments, several mg of soluble, human HGF were first produced and purified from stable clones of HEK293 cells that were grown in 5% serum (FIG. 12A). Importantly, the recombinant HGF produced by this method was 100% processed by factors contained in serum (e.g. HGF-activating factor) as indicated by complete cleavage of the 90 kDa HGF protein into its subunits under reducing conditions (FIG. 12A). Activity of HGF was further confirmed by performing an ELISA to measure activated c-Met receptor after exposure of human cells (FIG. 10). For protection assays, 100 ng/ml of HGF was added to cells as HGF/IgG complexes or as free HGF combined with a concentration of IgG that matched that of the HGF/IgG complexes under comparison. A significant increase in protection conferred by HGF/IgG complexes was observed compared with uncomplexed HGF and IgG at individual, matched protein concentrations (p≤0.01, n=4; FIG. 12B). Therefore, uncomplexed HGF and IgG mixture were chosen as appropriate control for HGF/IgG complexes in subsequent experiments.

To determine if HGF/IgG complexes mediated their protective effects via a receptor (or receptors) that differed from c-Met, a second phospho-receptor tyrosine kinase (RTK) array was performed with lysates of human coronary artery endothelial cells that were incubated for 30 minutes in HGF/IgG complexes or a matched concentration of HGF combined with IgG. Of special interest, phosphorylation of receptor-like tyrosine kinase (RYK) (a.k.a. related to tyrosine kinase) was observed after treatment with HGF/IgG complexes, but not after treatment with free HGF and IgG (FIG. 12C). Receptor-like tyrosine kinase (RYK) is an "orphan" receptor tyrosine kinase with no ligand yet identified that promotes its phosphorylation. The level of c-Met phosphorylation was comparable in both the treatment groups, suggesting an additional mechanism for protection mediated by HGF/IgG complexes (FIG. 12C). Accordingly, a cell protection assay was performed next under conditions of simulated ischemia in the presence or absence of receptor-like tyrosine kinase (RYK) neutralizing antibodies. Blocking receptor-like tyrosine kinase (RYK) on coronary artery endothelial cells significantly decreased the protective effect of the HGF/IgG complexes (anti-RYK antibody, 2 ug/ml) (MEM 100±5.92, complexed HGF with anti-RYK 187.03±4.35, complexed HGF with species control Antibody 204.46±5.98 p≤0.01; FIG. 12D), but not the protection conferred by uncomplexed HGF with IgG (p=0.09; FIG. 12D).

Example 7: HGF/IgG Complexes Localize to Blood Vessels and Promote Vascular Protection after Myocardial Ischemia To test whether treatment by HGF/IgG complexes was advantageous over uncomplexed HGF with IgG in vivo, the relative level of vascular integrity after myocardial ischemia was compared with reperfusion. HGF (10 µg/ml) was mixed with non-specific polyclonal rat IgG (carrier) either in a complexed form or uncomplexed form and compared effects to MEM administration. 1 ml of HGF/IgG complexes or uncomplexed HGF with IgG (control) was then administered to 2 groups of rats at the time of reperfusion, 2 hours after left anterior descending coronary artery (LAD) occlusion (steady injection of treatment with a 30 gauge needle into left ventricle lumen at the apical end of heart). By FITC-albumin assay, treatment with HGF/IgG complexes significantly improved vascular integrity at 24 hours after ischemia-reperfusion when compared with results obtained for treatment with free HGF and IgG or with MEM (MEM, 544.1%±94.18 of sham, n=4; Complex, 370.2%±102.86 of sham, n=11; free HGF, 516.5%±53.93 of sham, n=8; p≤0.001; FIG. 12E). Immunohistochemistry using an antibody targeting the N-terminal His-tag of our recombinant HGF demonstrated a specific perivascular localization of His (HGF) when administered as HGF/IgG complexes. The complexes appear to localize near large vessels and also in the microvasculature within the infracted region (FIGS. 12F1, 12F2, and 12F3).

In the present study unique HGF/IgG complexes were identified that have not been reported previously. Without being bound by theory it is likely that this is the first "ligand" capable of inducing receptor-like tyrosine kinase (RYK) phosphorylation. Exposure of vascular endothelial cells to either HGF/IgG complexes or free HGF promoted the phosphorylation of c-Met to the same extent, but only HGF/IgG complexes were able to induce phosphorylation of receptor-like tyrosine kinase (RYK). Furthermore, protection of endothelial cells by HGF/IgG complexes was substantially diminished when receptor-like tyrosine kinase (RYK) was blocked by neutralizing antisera. At present, the intracellular signaling cascade downstream of receptor-like tyrosine kinase (RYK) phosphorylation has yet to be determined, but many reports describe receptor-like tyrosine kinase (RYK) as a modulator of Wnt ligands and Wnt signaling. Receptor-like tyrosine kinase (RYK) has also been shown to associate with Ephrins, which have known roles in vascular permeability during developmental angiogenesis and after injury. In the case of reperfusion injury and endothelial cell protection, receptor-like tyrosine kinase (RYK) signaling may promote intracellular signal transduction that directly increases cell survival. Mechanistic studies on the role of receptor-like tyrosine kinase (RYK) in endothelial cell protection and reperfusion injury after myocardial ischemia will benefit from small molecule chemical inhibitors and/or transgenic tools that are currently unavailable.

HGF/IgG complexes have potential as a new translational strategy to provide enhanced, localized protection to sites of vascular injury. Recombinant human HGF and IgG was found to interact in a predictable manner in vitro, and, could be prepared reproducibly for in vivo administration. Compared with free HGF, HGF/IgG complexes provided superior preservation of vascular integrity in a clinically-relevant model of myocardial ischemia with reperfusion. Immunohistochemical data indicated that HGF/IgG complexes localized to blood vessels in a different fashion than did free HGF, both spatially and temporally; this may increase local concentration and/or retention time, thereby enhancing its protective effect(s). In addition to myocardial ischemia, other forms of tissue injury or disease that involve damage to the endothelium, such as stroke and peripheral artery disease, may also benefit from treatment with HGF/IgG complexes.

The experiments above were performed with the following methods and materials.

Human Epicardial Derived Cell-Conditioned Medium (EPI CdM)

Conforming with the principles outlined in the Declaration of Helsinki, and with patient's informed consent, right atrial appendages were obtained during cardiac bypass surgery. The right atrial biopsies were used to derive primary cultures of human epicardial-derived cells. After epithelial to mesenchymal transformation, passage 2 human epicardial-derived cells were seeded and grown in 150 cm$^2$ dishes (NUNC®) in Claycomb base medium supplemented with 10% FCS (lot selected for rapid growth of human mesenchymal stem cells, Atlanta Biologicals, Lawrenceville, Ga.), 100 units/ml penicillin, 100 µg/ml streptomycin, and 2 mM L-glutamine (Mediatech Inc., Hendron, Va.). When the cells reached 80-90% confluence, the plates were washed twice with PBS and serum-free MEM (MEM) was placed on the cells (20 ml per plate). After 48 hours of incubation, the human epicardial-derived cell-conditioned medium was collected, filtered (0.2 µm PES membrane, NALUENE® MF75, Rochester, N.Y.), and concentrated to 10-fold or 30-fold with a LABSCALE® TFF diafiltration system with the use of filters with a 5 kD cut-off (Millipore, Bedford, Mass.) or with AMICON® CENTRICON® filters (Millipore) with a 5 kD cut-off. One ml vials of Conditioned Medium were frozen and stored at −80° C. Some of the human epicardial-derived cell-conditioned medium was kept at 1× (unconcentrated) for ELISAs and cell protection assays with primary human cardiac endothelial cells. ELISAs for human growth factors were performed with commercially available kits (R and D systems).

Myocardial Ischemia-Reperfusion Surgery and Treatment with Human Epicardial-Derived Cell-Conditioned Medium All animal procedures conformed to the Guide of the Care and Use of Laboratory Animals published by the US National Institutes of Health (NIH publication No. 85-23, revised 1996) and to the IACUC guidelines for animal care approved by the University of Vermont. Fischer 488 rats (males, 7 weeks of age) were weighed, shaved, anesthetized under 4% isoflurane, and endotracheally-intubated. Rats were ventilated at a respiration rate of 65 beats per min under a peak inspiration pressure of 15 cm H2O (Kent Scientific). Body temperature was maintained at 37° C. with a heated pad (Gaymar). Through a dermal incision, a blunt dissection of the fascia was performed and the intercostal muscles were separated. The heart was exposed by retraction of the pericardium to expose the left anterior descending coronary artery (LAD). The left anterior descending coronary artery (LAD) was then encircled with 6-0 nylon suture. To facilitate release of suture at the time of reperfusion, a 0.4 cm length of PE10 tubing was placed over the left anterior descending coronary artery (LAD). The left anterior descending coronary artery (LAD) was then occluded; this was confirmed by blanching of the anterior free wall of the left ventricle. Animals were allowed to recover off the ventilator. After 2 hours, the rats were re-intubated under anesthesia, ventilated, and the chest wall was re-opened. Hearts were exposed to reveal the suture, which was released, and reperfusion was visually confirmed by blood flow through the left anterior descending coronary artery and "re-pinking" of the blanched area. For each rat, 1 ml of MEM or human epicardial-derived cell-conditioned medium or other pure factor treatments were steadily injected over a period of 1.5 min through left ventricle wall into the ventricle lumen (intra-arterial, 30.5 gauge needle). After the injection, the chest wall was closed and the rats recovered in their cages for 24 or 72 hours prior to euthanization and tissue harvest. Under anesthesia, the chest of sham-operated animals was opened (twice) to visualize the intact pericardium, corresponding to the times of ischemia and reperfusion surgeries. No further manipulations or treatments were performed on the sham animals.

Measurement of Vascular Permeability In Vivo

At 22 hours post-ischemia, animals were injected with 0.5 ml Fluorescein isothiocyanate labelled bovine Serum (FITC)-albumin (tail vein, 5 mg/ml). After 2 hours, rats were anesthetized, perfused with 50 ml sterile PBS to wash out circulating FITC-albumin from blood vessels, and whole hearts were excised into sterile PBS. To isolate the left ventricles with septum, the adventitial tissue, major vessels and left and right atria were separated. Hearts were then homogenized in PBS (2 ml/gm wet weight of tissue) using a POLYTRON® dispersing tool (EURO TURRAX® T206 IKA Labortechnik; Dispersing Tool S25N-10G, outer diameter 10 mm; IKA Works Inc., Wilmington, N.C., USA) and centrifuged at 16,000×g for 20 min. The soluble fraction was separated and 100 µl volumes were aliquoted to determine the amount of FITC extravasated into myocardial tissue. Fluorescence readings were measured in duplicate at 480 nm excitation and 520 nm emission wavelengths on a HT Synergy plate reader (BIOTEK® Instruments, Winooski, Vt.).

Preparation of HGF/IgG Complexes

Recombinant human HGF was diluted to a working concentration of 10 µg/ml in sterile PBS. Mixed polyclonal IgG (non-specific) from human serum was diluted to 14 µg/ml. The IgG was mixed with diluted HGF in a total volume of 10 ml (1:1 molar ratio; HGF:IgG). The mixture was then concentrated 40-fold (from 10 ml to 250 µl) using a CENTRICON® device (CENTRICON® Plus-70 Centrifugal Filter, ULTRACEL®-PL Membrane, 30 kDa Millipore). This concentrated mixture was diluted in PBS to give final doses of 1× or 10×HGF:IgG mix. Different concentrations of HGF were then used for treatment studies either in pure form or as HGF/IgG complexes.

Statistical Analysis

Comparisons of data from individual control and treatment groups were made by 2-tailed Student's t test. Values of $p \leq 0.05$ were considered statistically significant. For studies with comparison of multiple groups or time points were ANOVA with Bonferroni post-hoc testing. Values of $p < 0.05$ were considered statistically significant.

Isolation of Adult Human Epicardial Progenitor Cells Undergoing Epithelial to Mesenchymal Transformation into Precursor Cells Right atrial appendages were obtained from consenting cardiac bypass patients in a protocol that was approved by the IRB of the University of Vermont. The appendages were transferred from the hospital to the UVM Stem Cell Core on ice in 50 ml conical tubes containing explant medium: Alpha MEM (Invitrogen, Carlsbad, Calif.), 10% FCS (Atlanta Biologicals, Lawrenceville, Ga.), 100 units/ml penicillin, 100 µg/ml streptomycin, and 2 mM L-glutamine (Mediatech Inc., Hendron, Va.).

Method #1

In a cell culture hood, appendages were immediately rinsed in 1×PBS and any extracardiac fat was manually removed with fine scissors. The remaining tissue was transferred to a 100 cm² dish) containing 1×PBS supplemented with 1 mg/mL collagenase/dispase (Roche Applied Science, Indianapolis, Ind.) in which it was minced into approximately 1 mm³ pieces with sterile scalpel blades. The dish was placed into a sterile 37° C. humidified cell culture incubator for 1.5 hours, with shaking every 10 minutes. The resulting tissue digest was collected and centrifuged at 600×g for 5 min. The pellet was resuspended and washed in 25 ml of explant medium and centrifuged again. The final pellet was resuspended in 20 ml of explant medium and the digested fragments were split between 2 uncoated 100 cm2 dishes. After 2-3 days, the dishes were supplemented by the addition of 5 ml of explant medium and then left undisturbed to allow for the adherence of tissue fragments. After 5-7 days, when fibroblast outgrowth from the explants had almost reached confluence, the dishes were washed once by PBS and the explant medium was changed to a medium that favored stem/progenitor cell growth: DMEM/F12 with 3% FCS and 20 ng/ml epidermal growth factor (EGF), 10 ng/ml basic fibroblast growth factor (bFGF), 10 ng/ml leukemia inhibitory factor (LIF) (all growth factors from Sigma, Saint Louis, Mo.), 1×ITS plus (BD Biosciences, San Jose, Calif.), 100 units/ml penicillin, 100 µg/ml streptomycin, and 2 mM L-glutamine. After 2-3 days, areas of epicardial progenitor cells could be observed to be proliferating in between the fibroblasts. The progenitor cells were morphologically distinguishable from surrounding cell types, did not mix with surrounding cells, and formed floating spheroids and cell aggregates that resembled bunches of grapes as they divided upwards into the medium rather than horizontally. By shaking the dishes and washing once with calcium- and magnesium-free PBS, the floating progenitor cells were collected. The resulting cells (epicardial progenitor cells) were cultured in petri dishes (uncharged) in stem/progenitor growth medium for up to several weeks (in some cases up to 2 months). The epicardial nature of the cells was clear as all of the cells were epithelial and expressed Keratin proteins. Under these conditions, the epithelial cells continued to produce floating cells. To induce epithelial to mesenchymal transformation, the epicardial cells were collected, centrifuged at 600×g for 5 min, resuspended in Claycomb medium (SAFC Biosciences, Sigma) with 10% FCS, 100 units/ml penicillin, 100 µg/ml streptomycin, and 2 mM L-glutamine, and transferred to new dishes. Following adherence to culture plastic, the majority of the progenitor-like cells underwent epithelial to mesenchymal transformation within 3 days into precursor cells and expanded rapidly in the Claycomb medium with 10% FCS.

It was examined whether long-term growth in the stem/progenitor cell medium (low serum with growth factors) and in uncoated petri dishes was necessary to generate the precursor cells at the next stage of culture. This was not the case as primary floating epithelial progenitor cells obtained directly from initial feeder layer cultures could also undergo epithelial to mesenchymal transformation when plated onto typical positively-charged cell culture dishes and incubated in the Claycomb medium with 10% FCS.

Method #2

Epicardial explants were cultured for up to 7 d in explant medium to allow outgrowth of epithelial cells. Upon switching to the adult stem/progenitor medium as above, the epithelial cells similarly became refractile and formed spheres and "bunches of grapes". These progenitor-like cells also expressed Keratins and could be induced to undergo epithelial to mesenchymal transformation into human epicardial derived cells in Claycomb medium containing 10% FCS (as above) (pictured in FIG. 2).

Characterization of Cell Surface Epitopes

Pellets containing 0.5×106 to 1×106 cells were suspended in 0.5 ml PBS and were incubated for 30 min at 4° C. with monoclonal mouse anti-human antibodies that were pretitered for flow cytometry. All antibodies except those against CD105 and NG2 (Beckman Coulter, Miami, Fla.) were purchased from BD Biosciences Pharmingen (San Diego, Calif.). After labeling, the cells were washed twice with PBS and analyzed by closed-stream flow cytometry (LSR II, Becton Dickinson, Franklin Lakes, N.J.).

Immunoblotting

The soluble fraction from above was diluted 1:1 in protein lysis buffer (20 mM Tris, pH 7.4; 1 mM EDTA; 10 mM Sodium Chloride; 0.5% v/v Triton X-100) containing protease inhibitor (Complete mini #04693116001, Roche, Basel, Switzerland) and phosphatase inhibitor (P0044-1ML, Sigma). Protein concentration was determined with a commercial Lowry assay (BioRad DC Protein Assay). For each sample, 10 µg of protein was loaded on a 4-12% Bis-Tris gel (Invitrogen). Proteins were transferred to a PVDF membrane and blocked in 5% non-fat dry milk in TPBS for 1 hour at room temperature. Primary antibodies were diluted in 5% non-fat dry milk and incubated with membranes overnight at 4° C.: phosphoVE-Cadherin (44-1144G pTyr658, Invitrogen; 1:500), α-smooth muscle actin (A5228 clone 1A4, Sigma Aldrich; 1:1000), and GAPDH (Clone 6C5, Chemicon, Millipore; 1:1000). Membranes were washed in TPBS for 10 min×3 and incubated in HRP-conjugated secondary antibodies for 1 hour at room temperature. Membranes were washed for 15 min×3 and signals were enhanced by chemiluminiscence (Perkin Elmer) prior to exposure on X-ray film (Kodak).

Immunohistochemistry and Immunocytochemistry Assays

Cells cultured in chamber slides were washed once with PBS and fixed by 10 min incubation in 4% paraformaldehyde in PBS. Following several PBS washes, the chamber slides were blocked for 1 hour with 5% goat serum with 0.4% Triton-X 100 in PBS. Primary antibodies were diluted into blocking solution, placed on the cells, and incubated overnight at 4° C. The following primary antibodies were used: Smooth muscle myosin heavy chain, (SMMS-1, Dako, Carpinteria, Calif. 1:100), Von Willebrand Factor (F8/86, Dako 1:50), Fibroblast (prolyl hydroxylase) (clone 5B5, Dako 1:100), GATA 4 (G-4, Santa Cruz Biotechnology, Santa Cruz, Calif. 1:100) Cytokeratin (C2562, Sigma 1:100), Epicardin (TCF21, ab32981, Abcam; 1:100), Vimentin (E2944, Spring Bioscience, Freemont, Calif. 1:200) WT1 (C-19, Santa Cruz Biotechnology 1:100), RALDH2, (Bioss, bs-3676R 1:200). Following 3×PBS washes, secondary antisera was applied in blocking buffer and incubated for 1 hour at RT. After 3 more washes, slides were mounted (Vectashield with DAPI, Vector laboratories, Burlingame, Calif.), cover slips were applied, and specimens were viewed with an epifluorescence microscope (Leica DM6000B with DFC350 FX camera). Immunohistochemistry was performed as described previously (Iso et al., *Stem Cells*. 2013; 32:674-83). Hearts were isolated and fixed overnight in 4% paraformaldehyde. They were then equilibrated in 15 and 30% sucrose consecutively (24 hours in each) followed by mounting in OCT. Hearts were sectioned in 10 μm serial sections, apex to base. Fixed slides were heated on a heated block for 20 minutes at 52° C. and washed 2×5 minutes in PBS. Slides were blocked in goat serum (5% goat serum, 0.05% Triton X100 in PBS) for 1 hour at room temperature followed by incubation in primary antibody overnight; mouse anti rat CD31 (1:50, BD Bioscience). The following day, slides were washed 2×5 minutes in PBS, and incubated in Alexa 594 conjugated goat anti mouse antibody. Slides were treated with 20 μg/ml Proteinase K in PBS for 15 minutes at room temperature and washed thoroughly with PBS 2×5 minutes. Slides were incubated in equilibration buffer for 1 minute at room temperature followed by incubation in working enzyme solution with substrate for 1 hour at 37° C. They were then washed in stop/wash buffer for 10 minutes at room temperature followed by mounting with DAPI and mounting medium.

RT-PCR

Total RNA was isolated from cell pellets with a commercial kit (RNAQUEOUS®, Ambion, Austin, Tex.). To avoid the possibility of contaminating DNA, the total RNA samples were treated with DNase prior to reverse transcription (TURBO DNASE®, Ambion). Reverse transcription was performed with Superscript III (Invitrogen) in the presence of RNase inhibitor (RNASEOUT®, Invitrogen). PCR was carried out with an EPPENDORF® MASTER CYCLER® EP thermal cycler. Control RT-PCR reactions included template samples in which the reverse transcriptase was omitted from the single strand synthesis reaction. Primer sequences and annealing temperatures are listed below. Target sequences were denatured at 94° C. (2 min) followed by 30 amplification cycles of 94° C. (30 s), anneal temp (30 s), and 72° C. (45 s). The last PCR step extended the products at 72 C for 1 min. RT-PCR products were analyzed on 1% agarose gels. The following PCR primers were used: SNAIL, Forward 5' TTT ACC TTC CAG CAG CCC TA 3', Reverse 5' CCC ACT GTC CTC ATC TGA CA 3'; SLUG, Forward 5' GAG CAT ACA GCC CCA TCA CT 3'Reverse 5' GGG TCT GAA AGC TTG GAC TG 3'; TWIST, Forward 5' GTC CGC AGT CTT ACG AGG AG 3', Reverse 5' TGG AGG ACC TGG TAG AGG AA 3'; SMAD1, Forward 5' CTA CCC TCA CTC TCC CAC CA 3', Reverse 5' GCA CCA GTG TTT TGG TTC CT 3'; GATA5 Forward 5' CAC AAG ATG AAT GGC GTC AA 3' Reverse 5' CTT CCG TGT CTG GAT GCT TT 3'; Wt1 Forward 5' CGG GGG TGA ATC TTG TCT AA 3' Reverse 5' CCT GGA CCA TCC CCT ATT TT 3'; Isl-1, Forward 5' GTA GAG ATG ACG GGC CTC AG 3', Reverse 5' TTT CCA AGG TGG CTG GTA AC 3'; Tbx18 Forward 5' GGG GAG ACT TGG ATG AGA CA 3', Reverse 5' AGC AAG AGG AGC CAG ACA AA 3'; Tbx5 Forward 5' ACG TGC TCA GTT TTG CCT CT 3', Reverse 5' CAG TTT TGT GTT GGC ATT GG 3' alpha smooth muscle actin (a SMA) Forward 5' GAA GAG GAC AGC ACT GCC T 3' Reverse 5' CTG ATA GGA CAT TGT TAG CAT A 3' von Willebrand Factor (vWF) Forward 5' AAG AAC CGA AGT CCC AGG AGA AAG G 3', Reverse 5' AGA TTT CAG AGG CGT TCT AAA ACT CA 3' GATA4 Forward 5' GAC GGG TCA CTA TCT GTG CAA C 3', Reverse 5' AGA CAT CGC ACT GAC TGA GAA C 3'; Mef2C Forward 5' CTG GGA AAC CCC AAC CTA TT 3', Reverse 5' GCT GCC TGG TGG AAT AAG AA 3' Myocardin Forward 5' GGA CTG CTC TGG CAA CCC AGT GC 3', Reverse 5' CAT CTG ACT CCG GGT CAT TTG C 3' GAPDH Forward 5' GCT GAG TAC GTC GTG GAG T 3', Reverse 5' CAC CAC TGA CAC GTT GGC A 3'.

Pull Down of HGF from Human Epicardial-Derived Cell-Conditioned Medium

Monoclonal goat anti-human HGF (R & D Systems) was incubated with 30× human epicardial-derived cell-conditioned medium overnight at 4° C. on a rocking platform. The following day, 1 ml of human epicardial-derived cell-conditioned medium was incubated with 250 μl of Streptavidin agarose (GE Healthcare) for 2 hours at 4° C. on a rotating platform. The agarose beads were washed twice thoroughly with PBS to remove traces of ethanol from the stock preparation. After incubation the beads with human epicardial-derived cell-conditioned medium were centrifuged at 4° C. for 30 minutes at 800× g to collect the "pull down" fraction that had separated with the pelleted beads. Sandwich ELISA (R & D Systems) was performed on human epicardial-derived cell-conditioned medium after pull down to confirm depletion of HGF).

Recombinant Human HGF

A recombinant human HGF (HGF) expression plasmid was constructed by cloning a human HGF cDNA from plasmid pBabe-puroHGF (B. Weinberg Lab, Addgene, #10901) into vector pIRES-puro3 (Clonetech), with the addition of 6×His Tag to the C-terminus. The plasmid was introduced into HEK293 cells by transfection (LIPOFECTAMINE® 2000, Invitrogen) with puromycin selection of stable clones. For production of recombinant HGF, cells were grown in 150 mm$^2$ dishes in DMEM containing 5% FBS with medium changes every 3-4 days. For purification, medium containing secreted and processed HGF was clarified by 3 min centrifugation (2934 g) and ultrafiltration. Heparin-sepharose affinity chromatography (GE Healthcare) was used as 1 step of purification. Heparin-bound factors were eluted stepwise with 1 M NaCl, diluted, and applied onto Ni-NTA Resin (Novagen). HGF was eluted with 250 mM of imidazole (~95% purity of hHGF by SDS-PAGE).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An isolated HGF/IgG complex comprising recombinant human HGF and human non-specific IgG.

\* \* \* \* \*